US012636388B2

(12) United States Patent
Stager et al.

(10) Patent No.: US 12,636,388 B2
(45) Date of Patent: May 26, 2026

(54) FLEXIBLE DIFFUSE-REFLECTIVE SMART CHAMBER FOR EFFECTIVE TARGET DOSING OF COMPLEX PLANT SURFACES AND METHODS OF USE THEREOF

(71) Applicant: TRIC Robotics Inc., San Luis Obispo, CA (US)

(72) Inventors: Adam Stager, Newark, DE (US); Gordon McGregor, Landenberg, PA (US); Ryan Berard, Boston, MA (US)

(73) Assignee: TRIC Robotics Inc., San Luis Obispo, CA (US)

( * ) Notice: Subject to any disclaimer, the term of this patent is extended or adjusted under 35 U.S.C. 154(b) by 0 days.

(21) Appl. No.: 18/686,825

(22) PCT Filed: Aug. 22, 2022

(86) PCT No.: PCT/US2022/041116
§ 371 (c)(1),
(2) Date: Feb. 26, 2024

(87) PCT Pub. No.: WO2023/034066
PCT Pub. Date: Mar. 9, 2023

(65) Prior Publication Data
US 2024/0382634 A1     Nov. 21, 2024

Related U.S. Application Data

(60) Provisional application No. 63/238,650, filed on Aug. 30, 2021.

(51) Int. Cl.
*A61L 2/00*     (2006.01)
*A61L 2/10*     (2006.01)
(Continued)

(52) U.S. Cl.
CPC .................. *A61L 2/10* (2013.01); *A61L 2/24* (2013.01); *A61L 2103/05* (2026.01);
(Continued)

(58) Field of Classification Search
CPC ...................................................... A01G 7/045
See application file for complete search history.

(56) References Cited

U.S. PATENT DOCUMENTS 4,045,911 A * 9/1977 Ware ...................... A01G 9/249
                                              47/DIG. 6
5,040,329 A * 8/1991 Michaloski ............ A01G 7/045
                                              47/DIG. 6
(Continued)

FOREIGN PATENT DOCUMENTS

JP          2014-200205 A     10/2014
WO     WO 2019/125807 A1     6/2019
WO     WO 2020/163716 A1     8/2020

OTHER PUBLICATIONS

International Search Report and Written Opinion in international patent application No. PCT/US2022/041116 mailed Dec. 20, 2022.
(Continued)

*Primary Examiner* — Christopher D Hutchens

(74) *Attorney, Agent, or Firm* — Fitch, Even, Tabin & Flannery LLP

(57)     ABSTRACT

Flexible diffuse-reflective smart camber (FDRSC) devices are disclosed herein. The devices include UV-C lights sources and an irradiance chamber. The irradiance chamber
(Continued)

is open on at least one end through which the plants to be treated are exposed to the UV-C irradiance. Further, the inner surfaces of the irradiance chamber are covered by or consist of a diffuse reflective material that passively intensifies and uniformly distributes the UV-C irradiance to penetrate plant canopies. Also described herein are autonomous vehicles for moving the FDRSC devices across fields of crops and other plants, which is controlled in real time by a dosing control system. Also described herein are methods of in-situ UV-C treatment of plants using the FDRSC devices.

25 Claims, 7 Drawing Sheets

(51) Int. Cl.
| | |
|---|---|
| *A61L 2/24* | (2006.01) |
| *A61L 103/05* | (2026.01) |

(52) U.S. Cl.
CPC ........ *A61L 2202/11* (2013.01); *A61L 2202/14* (2013.01); *A61L 2202/16* (2013.01)

(56) References Cited

U.S. PATENT DOCUMENTS

| | | | | |
|---|---|---|---|---|
| 7,875,862 | B1 * | 1/2011 | Hudson | A01M 21/04 |
| | | | | 250/492.1 |
| 10,434,208 | B1 * | 10/2019 | Ngo | A01G 9/249 |
| 10,694,681 | B2 * | 6/2020 | Topps | A01C 1/00 |
| 11,452,264 | B1 * | 9/2022 | Genga, Jr. | F21V 21/15 |
| 2006/0148071 | A1 * | 7/2006 | Bauer | C05F 17/964 |
| | | | | 435/290.1 |
| 2014/0043787 | A1 * | 2/2014 | Wang | F21V 13/08 |
| | | | | 362/84 |
| 2016/0374273 | A1 * | 12/2016 | Quazi | A01G 9/249 |
| | | | | 362/235 |
| 2017/0099826 | A1 | 4/2017 | Paoluccio et al. | |
| 2019/0021233 | A1 * | 1/2019 | Hamby | H05B 47/196 |
| 2019/0172986 | A1 * | 6/2019 | Lu | C23C 14/0641 |
| 2020/0053854 | A1 * | 2/2020 | Xu | H05B 45/22 |
| 2020/0053856 | A1 * | 2/2020 | Barber | H05B 47/105 |
| 2020/0288646 | A1 * | 9/2020 | Howe | A01G 7/045 |

OTHER PUBLICATIONS

International Preliminary Report on Patentability in international patent application No. PCT/US2022/041116 mailed Mar. 5, 2024.

* cited by examiner

UVC Sensor Values

FLEXIBLE DIFFUSE-REFLECTIVE SMART CHAMBER FOR EFFECTIVE TARGET DOSING OF COMPLEX PLANT SURFACES AND METHODS OF USE THEREOF

CROSS REFERENCES TO RELATED APPLICATIONS

This is a U.S. national filing, pursuant to 35 U.S.C. § 371, of International Application No. PCT/US2022/041116, filed Aug. 22, 2021, which claims benefit of the filing date of U.S. Provisional Application No. 63/238,650 filed Aug. 30, 2021, the entire content of each of which is incorporated by reference herein.

FIELD OF THE INVENTION

The present invention relates generally to treatment of plants. In particular, described herein is a device for in-situ treatment of plants with UV-C light that includes a diffuse-reflective irradiance chamber.

BACKGROUND OF THE INVENTION

With increasing population and decreasing available farmland, the need for efficient farming is more important than ever. According to the U.S. Census Bureau, the world population is projected to increase to 9 billion by 2044, while farmland acreage will continuously decline [Mayo, "Population Growing but US Farm Acreage Declining" in Ag in the News, Economics, Educational Training, Farm Succession, General Agriculture, Workshop IFAS Extension (Mar. 4, 2016)]. Increasing crop yields rely, in part, on protecting crops from diseases caused by pathogen and pest infestation, such as harmful fungi, bacteria, spider mites, mollicutes, viruses, protozoa, viroids, and other parasitic organisms.

Today famers rely mainly on either creating pest-resistant hybrid or genetically modified plants or the application of chemicals, Spinosad, or natural toxins for pest control on crops and other plants. The creation of hybrid plants with pest resistance is rather limited as this approach relies on the discovery and isolation of resistance traits within the plant population, whereas genetically modified plants that require introduction of foreign resistance genes are becoming more and more disfavored by the consuming public. Chemical treatments are unreliable due to resistances and increasing regulatory pressures, and are damaging to the environment, costly, and require hazardous human labor for application. Further, today's consumers have higher demands for non-chemically treated fruits and vegetables. Organic methods tend to be insufficiently effective to sustain the industry and are high risk for farmers. Thus, it is clear that more efficient and safe methods of pest and pathogen control are needed.

One method of pest control involves dosing plants with ultraviolet (UV) light. Treatment with UV light is not susceptible to resistances (i.e., it is abiotic), does not involve chemical application, reduces labor, and can be used reliably in the wind and rain. However, current methods of UV dosing tend to only treat the tops of leaves and fails to adequately penetrate the plant canopy to dose the lower areas of the plant and the bottoms of leaves. Thus, adequate UV-dosing requires placement of UV light-emitting lights on the ground or laterally in relation to the plants to sufficiently cover the plant canopy with the UV light treatment. However, such requirements are not practical for large scale field treatment or treatment of plants in a limited space (e.g., vertical farms and greenhouses). Further, current methods of UV dosing utilizing specular reflectors to intensify the UV emission result in non-uniform dosing on the plant canopy resulting in over-exposure on some plants and plant parts causing radiation damage while inadequately dosing other plants and plant parts.

Thus, there remains the need in the art for a plant pathogen-control system that enables uniform, efficient, and effective dosing of plant canopies without damaging plant tissue.

SUMMARY OF THE INVENTION

Described herein is a flexible diffuse-reflective smart chamber ("FDRSC") device capable of uniform, efficient, and effective in-situ UV treatment of plants. In particular, the FDRSC device disclosed herein includes UV-C light sources within an irradiance chamber, the inner surfaces of which comprise a diffuse-reflective material. Thus, when plants are received within or in close proximity to the irradiance chamber, the UV-C light emitted from the light sources is diffusely reflected and deflected off of the inner surfaces of the chamber, which intensifies the UV-C irradiance and exposes the plants to a uniform distribution of UV-C light. In this manner, the underside of the plant leaves and other regions within the plant canopy are more easily penetrated without the need for additional UV-C light sources or lateral placement. Thus, the innovative design of the FDRSC device provides for more efficient and effective pest and pathogen control for plants as compared to existing devices and techniques.

In one aspect of the invention, disclosed herein is a device for reducing or preventing a pest or pathogen infestation on a plant or plant part. The device may include one or more light sources, an array frame having a top surface and a bottom surface, a first diffuse reflective material, and one or more reflectors having an inner surface and an outer surface. The first diffuse reflective material is disposed on the bottom surface of the array frame and positioned between the bottom surface of the array frame and each of the one or more light sources, which light sources are configured to emit light having a spectral wavelength in the range from about 100 nm to about 280 nm. Further, each of the one or more reflectors comprise a second diffuse reflective material on at least the inner surface. In this embodiment, the bottom surface of the array frame and inner surface of each of the one or more reflectors form an irradiance chamber configured for diffuse reflection of light and that is open on at least one end for receiving one or more plants or plant parts. As such, the light emitted from the one or more light sources is diffusely reflected by the irradiance chamber and contacts the one or more plants or plant parts to reduce or prevent a pest or pathogen infestation on the one or more plants or plant parts.

In another embodiment, the first diffuse reflective material and the second diffuse reflective material are selected from the group consisting of non-absorbing powder, fibrous material, polycrystalline material, white diffusing paint based on barium sulphate, sintered polytetrafluoroethylene, expanded polytetrafluoroethylene (ePTFE), and any combination thereof. For instance, the first diffuse reflective material and the second diffuse reflective material may be ePTFE or may be coated with ePTFE. In another embodiment, the device includes at least two reflectors, wherein each reflector is attached to and extends from an end of the array frame to form an irradiance chamber with a top end, at least two sides, and at least one open end for receiving the plants or plant parts.

In one embodiment, the irradiance chamber comprises a bottom end for receiving the plants or plant parts and at least one open side for receiving the plants or plant parts. In yet another embodiment, the device includes at least four reflectors, wherein each reflector is attached to and extends from an end of the array frame to form an irradiance chamber with a top end, four sides, and an open bottom end for receiving the plants or plant parts. In yet another embodiment, the reflectors are flexible reflectors comprising rubber, flexible plastic, or cloth coated with the second diffuse reflective material. In still other embodiments, the reflectors are flexible reflectors comprising ePTFE.

The one or more light sources of the device may also be configured to emit ultraviolet C (UV-C) light having a spectral wavelength in the range from about 220 nm to about 230 nm, or about 250 nm to about 260 nm. For instance, the one or more light sources can be fluorescent germicidal lamps. In another embodiment, the device includes 2, 3, or 4 light sources. The device may also include at least one distance detector disposed on the bottom surface of the array frame and one or more light sensors disposed on the bottom surface of the array frame. In particular embodiments, the at least one distance detector is a stereo camera and/or the one or more light sensors are UV-C sensors.

In some aspects of the invention, the device includes or is in communication with a dosing control system, which comprises one or more user-defined dosing parameters and a dosing controller. These user-defined dosing parameters may be selected from the group consisting of dosing amount, target dosing, minimum dosing distance, minimum dosing time, and any combination thereof. Moreover, the dosing control system receives electrical signals from the at least one distance detector to create a treatment contour profile and receives electrical signals from the one or more light sensors to create an volumetric irradiance profile. As such, the dosing controller combines data from the treatment contour profile and data from the volumetric irradiance profile to create an irradiance heat map, and further converts data from the irradiance heatmap to determine treatment distance, treatment time, or both treatment distance and treatment time based on the user-defined dosing parameters.

In another embodiments, the first diffuse reflective material and the second diffuse reflective material are at least about 80% reflective of UV-C light. In other embodiments, the first diffuse reflective material and the second diffuse reflective material are at least about 90% reflective of UV-C light, or even at least about 95% reflective of UV-C light. In yet other embodiments, the first diffuse reflective material and the second diffuse reflective material are at least about 98% reflective of UV-C light.

In another aspect of the invention, the device described above is attached to a support member of an autonomous vehicle. In an embodiment, the autonomous vehicle is a land vehicle comprising one or more wheels, wherein the support member is further attached to an adjustable vertical mount on the autonomous vehicle. Further, in some embodiments, the autonomous vehicle comprises a central processing unit (CPU) configured to receive electrical signals from the dosing control system such that the treatment time is communicated from the dosing control system to the CPU of the autonomous vehicle to cause rotation of the wheels to increase or decrease in velocity; or the treatment distance is communicated from the dosing control system to the CPU of the autonomous vehicle to cause the adjustable vertical mount to raise or lower the device; or both.

Another aspect of this disclosure features a method of treating or preventing pest or pathogen infestation on a plant or plant part that includes the steps of: a) providing the plant or plant part; b) placing the device as described above over the plant or plant part such that the plant or plant part is received within the irradiance chamber of the device; and c) contacting the plant or plant part with UV-C light emitted from the one or more light sources of the device at a target dosage amount for a period of time. In this aspect, the contacting of the plant or plant part with the UV-C light reduces or prevents infestation from pests or pathogens.

In one embodiment of the method, the pest or pathogen is selected from the group consisting of fungi, bacteria, insects, mollicutes, viruses, protozoa, viroids, and any combination thereof. For example, the pest or pathogen can be mildew or spider mites. In another embodiment, the plant or plant part is selected from the group consisting of asparagus, barley, beans, beets, blueberries, broccoli, cabbage, canola, cauliflower, celery, cranberries, corn, cotton, feed grains, flowers, garlic, grapes, lentils, lettuce, mushrooms, oats, peanuts, peas, peppers, potatoes, pumpkins, rice, sorghum, soybeans, spinach, squash, strawberries, sugar cane, sweet potatoes, tobacco, tomatoes, turnips, watermelon, and wheat.

In a particular embodiment of the method, the target dosage is at least about 1 $J/m^2$, or at least about 5 $J/m^2$. In another embodiment, the plant or plant part is contacted with the UV-C light for at least about 1 sec, or for at least about 5 sec. In another embodiment, the UV-C light has a spectral wavelength in the range from about 220 nm to about 230 nm, or about 250 nm to about 260 nm. In some aspects of the method, the pests or pathogens are reduced by at least 10% following contact of the plant or plant parts with the UV-C light for the period of time. In others, the pests or pathogens are reduced by at least 20% following contact of the plant or plant parts with the UV-C light for the period of time. The method described herein may be performed once, or it may include a contacting step that is repeated every day for at least about 1 week. In some embodiments, the contacting step is performed at night. In other embodiments, the contacting step is followed by a dark period.

One embodiment of the method includes the step of measuring one or more parameters of pest or pathogen infestation. In such embodiment, the measuring step is prior to, following, or both prior to and following the contacting step. For instance, the one or more parameters of pest or pathogen infestation may be selected from the group consisting of leaf rust, stem rust, sclerotinia, spots, damping, chlorosis, lesions, bacterial oozing, fruit rust, cankers, crown galls, Sheperd's crook stem ends, mosaic leaf patters, crinkled leaves, yellowed leaves, plant stunting, mycelium growth, mold growth, fruiting bodies, bacterial odors, stem rot, blight, fungal rings, water soaking, bacterial streaming, stunted growth, and wilting. In another embodiment, the measuring step is performed prior to and following contact, wherein a decrease in the one or more parameters indicates treating or preventing pest or pathogen infestation on a plant or plant part.

Another aspect of the invention features an autonomous vehicle for reducing or preventing a pest or pathogen infestation on a plant or plant part, wherein the autonomous vehicle includes the device as described above. In some embodiments, the autonomous vehicle is a drone or land vehicle. In others, the autonomous vehicle is used to treat or prevent pest or pathogen infestation on crops grown in a field.

Other features and advantages of the invention will be apparent by reference to the drawings, detailed description, and examples that follow.

DETAILED DESCRIPTION OF THE INVENTION

Figure 1A:
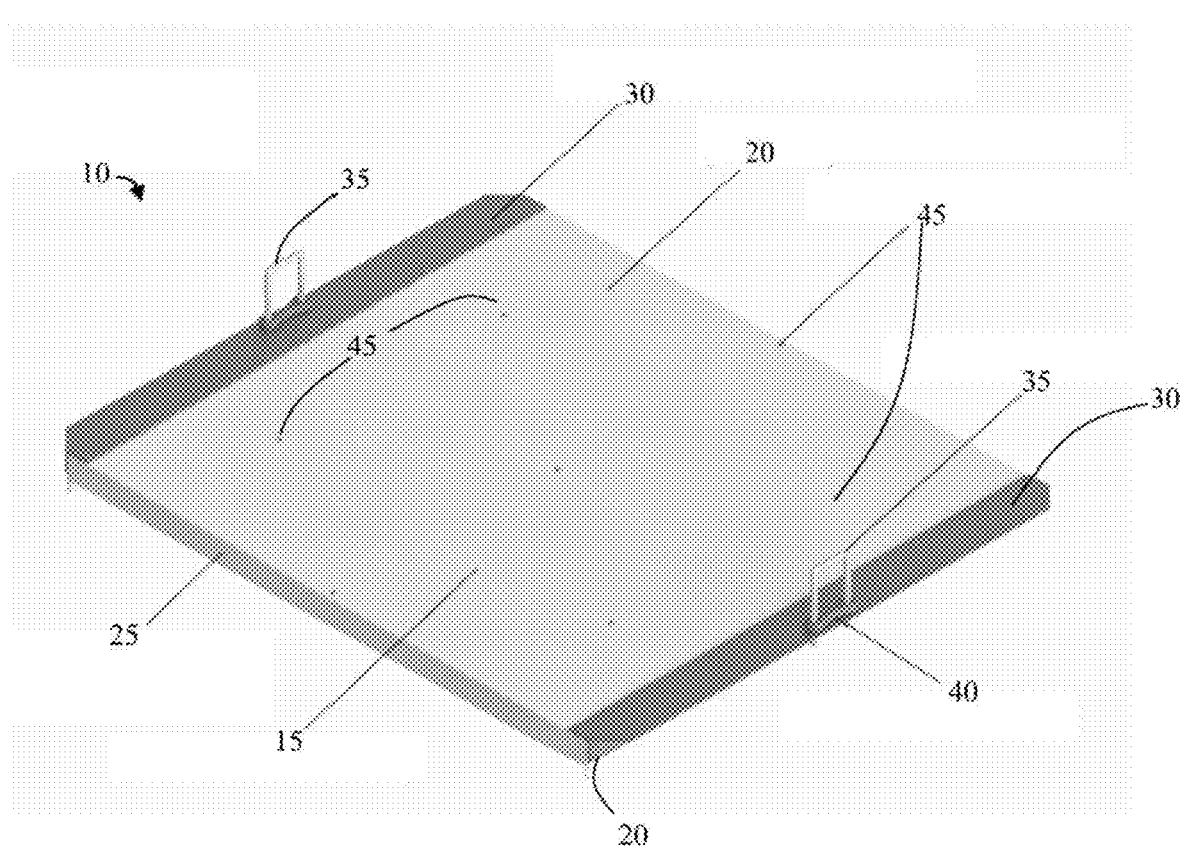
FIG. 1A is a top perspective view of an embodiment of the array frame of an exemplary FDRSC device.

The flexible diffuse-reflective smart chamber ("FDRSC") described herein enables in-situ treatment of plants with UV-C light. In particular, the FDRSC includes an irradiance chamber with at least one open end in which plants are received and exposed to UV-C irradiance emitted from one or more UV-C light sources. The FDRSC device will include at least one surface on which is disposed a diffuse-reflective material. In a preferred embodiment, each of the surfaces forming the interior of the irradiation chamber will be made from or otherwise be covered or coated in the diffuse-reflective material such that each inner surface of the chamber (except for at least one open end) is covered in diffuse-reflective material. As such, the UV-C light emitted from the UV-C light sources is deflected and reflected off of the chamber surfaces to uniformly intensify the UV-C irradiance within the chamber thereby penetrating plant canopies and applying irradiance coverage to plant parts deep within the plant canopy (e.g., the underside of leaves and parts shaded by the canopy). Moreover, the chamber can include flexible walls or reflectors to maintain the integrity of the diffuse-reflective chamber without damaging plants.

The FDRSC device can be anchored above the plants, moved across plants by way of a conveyor system, or moved across a field of plants by an autonomous vehicle or drone, which speed is controlled by a dosing control system being run on a computing device and works in combination with distance and irradiance sensors on the FDRSC to create an irradiance profile. This information can be used to determine whether particular target dosages are being applied and, if not, can signal to the central processing unit (CPU) of the autonomous vehicle to adjust the speed of movement, which, in turn adjusts the UV-C dosage being applied to the plants. Thus, the dosing control system includes a feedback loop that can adjust the UV-C dosage being applied to the plants in real time to ensure the target dosage is being achieved while preventing the likelihood of exceeding the plant damage threshold due to overexposure of UV-C.

The FDRSC device of the present invention can be used to treat a variety of plants having different plant canopy sizes, complexities, and densities in order to significantly reduce or eradicate pests or pathogens. This treatment can be applied daily, every other day, once a week, or any other period of time desired based on the plant to be treated and the pest or pathogen to be killed. In some embodiments, it is desirable to apply the UV-C treatment at night and to follow each treatment session with a dark period. The devices and methods will now be discussed in further detail.

Ranges, if used, are used as shorthand to avoid having to list and describe each and every value within the range. Any value within the range can be selected, where appropriate, as the upper value, lower value, or the terminus of the range.

The term "about" refers to the variation in the numerical value of a measurement, e.g., length, height, degrees, percentage, thickness, spectral wavelength, and the like, due to typical error rates of the device used to obtain that measure. In one embodiment, the term "about" means within 5% of the reported numerical value; preferably, it means within 3% of the reported numerical value.

As used herein, the singular form of a word includes the plural, and vice versa, unless the context clearly dictates otherwise. Thus, the references "a", "an", and "the" are generally inclusive of the plurals of the respective terms. Likewise, the terms "include", "including" and "or" should all be construed to be inclusive, unless such a construction is clearly prohibited from the context. Similarly, the term "examples," particularly when followed by a listing of terms, is merely exemplary and illustrative and should not be deemed to be exclusive or comprehensive.

The term "comprising" is intended to include embodiments encompassed by the terms "consisting essentially of" and "consisting of". Similarly, the term "consisting essentially of" is intended to include embodiments encompassed by the term "consisting of".

The term "adequate dosing" as used herein refers to the minimum amount of dosing required to kill or otherwise inactivate a pest or pathogen thereby reducing or eliminating the pest's or pathogen's negative economic impact on the plant's production.

The term "complex surfaces" as used herein refers to a combination of flat surfaces not contained on a single plane.

The term "dose" as used herein in connection with irradiation refers to the amount of irradiation on a surface over time, measured in Joules per meter squared (J/m$^2$). The term "coverage" when used herein in connection with "dose" or "dosing" means the percentage of total area receiving adequate dosing.

The term "diffuse reflection" as used herein refers to the reflection of irradiance from a surface such that a ray incident on the surface is scattered at many angles rather than at just one angle.

The term "in-situ treatment" is sometimes used herein to refer to the irradiation of a living plant.

The term "irradiance" as used herein refers to the amount of electromagnetic radiation reaching a surface measured in Watt per square meter (W/m$^2$). "Irradiance profile" as used herein refers to the irradiance values measured over a surface or volume.

The term "plant canopy" or "vegetative canopy" are used interchangeably herein to refer to the aboveground portion of a plant or crop, formed by the collection of individual plant stems, leaves, flowers, and other crown structures that grow outward in three dimensions.

The term "plant damage threshold" as used herein refers to the maximum amount of dosing a plant can withstand before causing a negative economic impact on the plant's production or yield.

The term "parameter" is used herein to refer to measuring pest or pathogen infestation or infection of a plant or plant part via any observable or measurable trait using suitable techniques available in the art that one having ordinary skill in the art would understand as indicative of pest or pathogen infestation or infection of a plant. A non-limiting list of "parameters" of pest or pathogen infestation include leaf rust, stem rust, sclerotinia, spots, damping, chlorosis, lesions, bacterial oozing, fruit rust, cankers, crown galls, Sheperd's crook stem ends, mosaic leaf patters, crinkled leaves, yellowed leaves, plant stunting, mycelium growth, mold growth, fruiting bodies, bacterial odors, stem rot, blight, fungal rings, water soaking, bacterial streaming, stunted growth, wilting, and the like.

The term "significantly reducing" as used herein with reference to pest or pathogen infestation means that the overall pest or pathogen infestation of the plant or plant part is at least 5%, preferably at least 10%, reduced compared to the pest or pathogen infestation on the plant or plant part prior to treatment or as compared to an equivalent plant or plant part that has not been treated.

The term "substantially equal" or "equidistant" as used interchangeably herein with reference to the distance between a plurality of objects means that the distance between any two objects is within 10% of the distance between any one of those objects with a third object; preferably the distance is within 5%.

The term "target dosing" as used herein refers to the range between adequate dosing and a plant's damage threshold.

The term "UV tolerant" as used herein to refer to a diffuse reflective material means that the material will not significantly degrade when exposed to UV light for an extended period of time. For instance, "UV tolerant" materials will not degrade by more than about 5% after exposure to UV-C light for at least about 100 hours; preferably, for at least about 500 hours.

EDRSC Device

The UV-C treatment of the present invention utilizes a FDRSC device that includes an irradiance chamber and that is open on at least one end and has at least one inner surface on which is disposed a diffuse reflective material. In a preferred embodiment, the irradiance chamber of the FDRSC device will include five diffuse reflective inner surfaces while being open at the bottom end for receiving the plant or plants to be treated. In other embodiments, the irradiance chamber of the FDRSC device is open at the bottom end and/or at least one side for receiving the plant or plants to be treated depending on the arrangement of crops and the type of crops to be treated. Additionally, two FDRSC devices can be used in combination wherein, optionally, each of the FDRSC devices is open at the bottom end and the side adjacent to the neighboring FDRSC device.

The FDRSC device will have one or more UV-C light sources disposed within the irradiance chamber configured to emit UV light to the plant or plants to be treated. As noted above, the FDRSC device utilizes the UV light for killing or controlling pests and pathogens (or reducing or inhibiting the ability of pests or pathogens to reproduce), including, but not limited to, fungi (e.g., mildew), bacteria, insects (e.g., spider mites), mollicutes, viruses, protozoa, viroids, and other parasitic organisms, on plants or plant parts. UV is a form of electromagnetic radiation with a spectral wavelength from about 10 nm to about 400 nm, which is below the visible light spectrum. UV exposure to plant surfaces can eradicate or significantly reduce harmful pests or pathogens on the leaves, stems, flowers, and other parts of the plant canopy. Of particular preference in the present device and method of use, is the use of UV light having a spectral wavelength of about 100 nm to about 350 nm, e.g., 100 nm, 105 nm, 110 nm, 115 nm, 120 nm, 125 nm, 130 nm, 135 nm, 140 nm, 145 nm, 150 nm, 155 nm, 160 nm, 165 nm, 170 nm, 175 nm, 180 nm, 185 nm, 190 nm, 195 nm, 200 nm, 205 nm, 210 nm, 215 nm, 220 nm, 225 nm, 230 nm, 235 nm, 240 nm, 245 nm, 250 nm, 255 nm, 260 nm, 265 nm, 270 nm, 275 nm, 280 nm, 285 nm, 290 nm, 295 nm, 300 nm, 305 nm, 310 nm, 315 nm, 320 nm, 325 nm, 330 nm, 335 nm, 340 nm, 345 nm, or 350 nm. In a preferred embodiment, the UV light is UV-C light having a spectral wavelength of about 100 nm to about 280 nm. In a particular embodiment, the UV-C light has a spectral wavelength of about 220 nm to about 230 nm, or about 250 nm to about 260 nm.

The UV light source can be generated using light sources available in the art, including, but not limited to, a mercury-vapor lamp, laser diode, LED light, fluorescent UV lamp, or any light source capable of emitting UV light with the appropriate spectral wavelength. Alternatively, a light source can be combined with an excitation light filter design to transmit only light having the desired UV spectral wavelength. In one particular aspect, the UV light source is generated from a fluorescent germicidal UV lamp configured to emit UV light having a spectral wavelength from about 100 nm to about 300 nm; preferably, from about 100 nm to about 280 nm. These UV light sources can be powered by any suitable means, such as via electrical connection to an external power source or by battery power. In one particular embodiment, the UV-C fluorescent lamps are powered by batteries in combination with an inverter and/or art-standard ballast. The power output of the UV-C light sources can be selected from any suitable power range, e.g., 45 W to about 60 W.

To kill or significantly reduce pests and pathogens on the plants, the plant surfaces may be exposed to UV-C irradiance for a sufficient period of time to achieve adequate dosing of the plant(s) or plant part(s). Surface coverage is a challenge on plants due to the tendency of plants to grow outward in three dimensions, generating a vegetative canopy with shaded regions not easily penetrated by the UV-C dosing. As such, current UV-C lamps are not suitable for in-situ treating of plants due to the complex surfaces of many vegetative canopies, which, in turn, leads to a failure to efficiently and uniformly dose the plant and achieve adequate dosing with UV-C irradiance. Therefore, current methods of in-situ treatment of plants with UV-C irradiance lack efficiency in significantly reducing or eliminating pest and pathogen infestation of the plant. The present FDRSC device overcomes these deficiencies by incorporating diffuse light reflecting materials to create a chamber capable of uniform and efficient UV-C irradiance that has better coverage than other devices existing in the art. As such, it is an object of the present invention to use the FDRSC device disclosed herein to apply in-situ UV-C treatment to plants for a period of time sufficient to achieve an adequate UV-C dosage without exceeding the plant damage threshold (e.g., due to UV-C overexposure).

In some embodiments, a sufficient period of time to achieve adequate dosing of the plant or plant part is at least 1 second, e.g., 1 sec, 2 sec, 3 sec, 4 sec, 5 sec, 6 sec, 7 sec, 8 sec, 9 sec, 10 sec, 11 sec, 12 sec, 13 sec, 14 sec, 15 sec, 16 sec, 17 sec, 18 sec, 19 sec, 20 sec, 21 sec, 22 sec, 23 sec, 24 sec, 25 sec, 26 sec, 27 sec, 28 sec, 29 sec, 30 sec, 35 sec, 40 sec, 45 sec, 50 sec, 55 sec, 60 sec, 2 min, 3 min, 4 min, 5 min, or more. In another embodiment, the period of time to achieve adequate dosing of the plant or plant part is less than about 5 minutes; preferably, less than about 3 minutes; more preferably, less than about 60 seconds. In another embodiment, the dosing of the plant is from about 15 sec to about 30 sec, or from about 15 sec to about 60 sec. In a preferred embodiment, the dosing of the plant is for at least 3 sec; more preferably, at least 5 sec. In some embodiments, the period of time to achieve adequate dosing of the plant or plant part is between about 3 sec and about 10 sec; preferably, between about 1 sec and about 5 sec. The period of time for the dosing can be selected to reach a desired target dose in the range from about 0.5 $J/m^2$ to about 30 $J/m^2$, e.g., 0.5 $J/m^2$, 0.6 $J/m^2$, 0.7 $J/m^2$, 0.8 $J/m^2$, 0.9 $J/m^2$, 1 $J/m^2$, 2 $J/m^2$, 3 $J/m^2$, 4 $J/m^2$, 5 $J/m^2$, 6 $J/m^2$, 7 $J/m^2$, 8 $J/m^2$, 9 $J/m^2$, 10 $J/m^2$, 11 $J/m^2$, 12 $J/m^2$, 13 $J/m^2$, 14 $J/m^2$, 15 $J/m^2$, 16 $J/m^2$, 17 $J/m^2$, 18 $J/m^2$, 19 $J/m^2$, 20 $J/m^2$, 21 $J/m^2$, 22 $J/m^2$, 23 $J/m^2$, 24 $J/m^2$, 25 $J/m^2$, 26 $J/m^2$, 27 $J/m^2$, 28 $J/m^2$, 29 $J/m^2$, or 30 $J/m^2$, depending on the area and density of the plant canopy. Preferably, the desired target dose is in the range from about 1 $J/m^2$ to about 20 $J/m^2$. For larger and denser plant canopies, the desired target dose is in the range from about 1 $J/m^2$ to about 1,200 $J/m^2$, e.g., 1 $J/m^2$, 10 $J/m^2$, 20 $J/m^2$, 30 $J/m^2$, 40 $J/m^2$, 50 $J/m^2$, 60 $J/m^2$, 70 $J/m^2$, 80 $J/m^2$, 90 $J/m^2$, 100 $J/m^2$, 200 $J/m^2$, 300 $J/m^2$, 400 $J/m^2$, 500 $J/m^2$, 600 $J/m^2$, 700 $J/m^2$, 800 $J/m^2$, 900 $J/m^2$, 1,000 $J/m^2$, 1,200 $J/m^2$, or 1,200 $J/m^2$. Preferably, the target dose is less than about 1,200 $J/m^2$; more preferably, it is less than about 750 $J/m^2$. For instance, the target dose for plants with dense plant canopies may be in the range from about 60 $J/m^2$ to about 750 $J/m^2$. In another embodiment, the desired target dose is at least about 0.5 $J/m^2$, e.g., 0.5 $J/m^2$, 0.6 $J/m^2$, 0.7 $J/m^2$, 0.8 $J/m^2$, 0.9 $J/m^2$, 1 $J/m^2$, 2 $J/m^2$, 3 $J/m^2$, 4 $J/m^2$, 5 $J/m^2$, 6 $J/m^2$, 7 $J/m^2$, 8 $J/m^2$, 9 $J/m^2$, 10 $J/m^2$, 11 $J/m^2$, 12 $J/m^2$, 13 $J/m^2$, 14 $J/m^2$, 15 $J/m^2$, 16 $J/m^2$, 17 $J/m^2$, 18 $J/m^2$, 19 $J/m^2$, 20 $J/m^2$, 30 $J/m^2$, 40 $J/m^2$, 50 $J/m^2$, 60 $J/m^2$ or more. For instance, in one exemplary embodiment, the target dose can be at least about 1 $J/m^2$, or at least about 5 $J/m^2$. In another exemplary embodiment the target dose is about 240 $J/m^2$.

In a preferred embodiment, the dosing of the plant by the UV-C irradiance is performed by an FDRSC device comprising one or more UV-C light sources, such as UV-C fluorescence lamps configured to emit electromagnetic radiation having a spectral wavelength in the range of from about 100 nm to about 280 nm. The FDRSC device will preferably constructed of multiple walls or barriers forming a chamber with at least one open end for receiving plants (see, for example, FIG. 1D). The chamber may include a top frame or array frame. The UV-C light sources are then disposed on the bottom surface of the array frame and configured to emit UV-C irradiance generally away from the bottom surface (i.e., generally downward). The array frame may be adapted to any desirable dimensions. In particular, the array frame is preferably planar having a length of about 5 in. to about 60 in. or more, e.g., 5 in., 10 in., 15 in., 20 in., 25 in., 30 in., 35 in., 40 in., 45 in., 50 in., 55 in., 60 in., or more; a width of about 5 in. to about 60 in. or more, e.g., 5 in., 10 in., 15 in., 20 in., 25 in., 30 in., 35 in., 40 in., 45 in., 50 in., 55 in., 60 in., or more; and a thickness of about 0.5 in. to about 10 in., or more, e.g., 0.5 in., 1 in., 1.5 in., 2 in., 2.5 in., 3 in., 3.5 in., 4 in., 4.5 in., 5 in., 5.5 in., 6 in., 6.5 in., 7 in., 7.5 in., 8 in., 8.5 in., 9 in., 9.5 in., 10 in., or more. For instance, in one embodiment, the array frame is about 20 in. to about 50 in. long, 15 in. to about 40 in. wide, and about 1 in. to about 5 in. thick. In the exemplary embodiment depicted in FIG. 1, the array frame is about 40 in. long, about 33 in. wide, and about 1.5 in. thick.

The array frame may be constructed of any suitable material that is sufficiently sturdy to provide support for the FDRSC device and relatively light weight, such as, but not limited to, plastic, aluminum, carbon, plaster, or a combination of these materials. For instance, the array frame of the FDRSC device may be constructed of a synthetic polymer, such as poly vinyl chloride (PVC) or white cellular PVC trim sheet material. For additional support, the array frame may include one or more support barriers made from the same or different material as the main body of the array frame. For instance, the array frame may contain a plurality of support barriers made from PVC material disposed on the bottom surface and in parallel and equidistant from each other (see, for example, FIG. 1B).

The array frame will have one or more UV-C light source disposed on the bottom surface. In one embodiment, the array frame has at least 2 UV-C light sources, e.g., 2, 3, 4, 5, 6, 7, 8, 9, 10 or more UV-C light sources. While any desired arrangement of the UV-C light sources is possible, it is preferred that the UV-C light sources will be disposed across the bottom surface of the array frame at substantially equal distances apart and arranged in parallel. For example, the array frame depicted in FIG. 1 includes 4 UV-C fluorescent lamps disposed in parallel and substantially equidistant to each other and equidistant to the parallel ends of the array frame. Further, in this particular embodiment, the UV-C fluorescent lamps alternate with the support barriers of the array frame, however, in other embodiments, the bottom surface of the array frame is substantially flat without any support barriers.

In order to produce uniform and intensified UV-C irradiance, the array frame will include a diffuse reflective material. Any material capable of diffuse reflection of UV light having a spectral wavelength from about 100 nm to about 300 nm, preferably from about 100 nm to about 280 nm, and which does not significantly degrade when exposed to UV light (i.e., UV tolerant) is suitable for use herein, including, but not limited to, non-absorbing powder (e.g., plaster), fibrous material (e.g., paper), polycrystalline material (e.g., marble), white diffusing paint based on barium sulphate, sintered polytetrafluoroethylene, expanded polytetrafluoroethylene (ePTFE), and the like. In some embodiments, the material capable of diffuse reflection of UV light is UV tolerant for at least about 100 hours; preferably, for at least about 500 hours. In others, the material may be very UV tolerant exhibiting less than 5% degradation after exposure to UV light for at least a cumulative total of about 1,000 hours over a period of six to eight months or more. The array frame can be coated in the diffusive material or draped/covered in thin sheets of diffusive material, or even coated with the diffuse material. In a preferred embodiment, a thin sheet or coating of ePTFE material is disposed on the bottom surface of the array frame. During assembly, the thin ePTFE sheet or coating having a thickness of about 0.1 mm to about 2 mm, e.g., 0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm. 1.3 mm, 1.4 mm, 1.5 mm, 1.6 mm, 1.7 mm, 1.8 mm, 1.9 mm, or 2 mm, is draped or coated over the bottom surface of the array frame. An ePTFE sheet can be attached to the support barriers by any suitable means, such as, but not limited to glue, tape, nails, screws, and the like. In some embodiments, the UV-C light sources can then be disposed over the ePTFE sheet portions and between the support barriers. This particular arrangement produces angled portions of the ePTFE sheet that taper towards either side of the UV-C lamps (see, for example, FIG. 1C). These angled portions of the ePTFE sheet form about 20° to about 40° angles, e.g., 20°, 25°, 30°, 35°, or 40° angles, relative to the bottom surface of the array frame; preferably the angles are about 20° to about 30° (e.g., about 25°). These angled portions serve to deflect UV-C irradiance away from the bottom surface of the array frame and away from the neighboring UV-C light sources in a diffuse and uniform manner. However, as one having ordinary skill in the art will appreciate, the diffuse reflective characteristics of the material enable diffuse reflection of UV-C light without requiring any angled surfaces. In other embodiments, for instance, there are no support barriers and no angled portions of the diffuse reflective material, but rather the diffuse reflective material is simply disposed across the bottom surface of the array frame.

In order to create a diffuse, uniform, and sufficiently intense chamber of UV-C irradiance, one or more flexible or semi-flexible reflector components can be attached to and extend down or away from the sides of the array frame to form, for example, an irradiance chamber open at one or more ends. Materials that are flexible or semi-flexible will preferably have a Modulus of Elasticity from about 0.001 to about 5 GPa. Preferably, the Modulus of Elasticity is less than about 0.5 GPA. The flexible reflectors can be made from any flexible material that has diffuse light reflecting properties or that is coated with a diffuse reflective material, it being understood that such diffuse material will also be capable of diffuse reflection of UV light and UV tolerant. For instance, the diffuse reflectors can be rubber, flexible plastic, cloth, or other material that is coated with a diffuse reflective material such as, but not limited to, non-absorbing powder, fibrous material (e.g., paper), polycrystalline material, white diffusing paint based on barium sulphate, sintered polytetrafluoroethylene, ePTFE, and the like. As with the diffuse reflective material discussed above in connection with the array frame, the flexible reflectors themselves can be made from diffuse reflective material, such as ePTFE. The flexible reflectors are typically attached to and extend down or away from each of four sides of the array frame to create a chamber that is open at the end opposite the array frame (see, for example, FIG. 1D). Alternatively, two or three flexible reflectors are attached to and extend down or away from two or three sides, respectively, of the array frame to form an irradiance chamber that is open at a bottom end and at least one side.

The FDRSC device is placed or moved over plants such that the plants are within the irradiance chamber or in close proximity to the irradiance chamber via the bottom opening or, in some embodiments, a side opening depending on the type of plant being treated or the arrangement in which the plants are being grown. Further, the bottom surface of the array frame and the inner surfaces of the flexible deflectors comprise diffuse reflective material such that the diffusion of the UV-C light within the FDRSC chamber causes a more uniform distribution of irradiance for plant surfaces within the FDRSC chamber. These diffuse reflective materials also "catch" UV-C light that would otherwise be reflected away from the plants and deflect that UV-C light back into the plant canopy. In this manner, the diffuse reflectors act as a passive, non-power-consuming source of irradiance thereby intensifying the UV-C dosage. The UV-C light emitted from the FDRSC device is less affected by damage, dirt, and other debris that tend to cause discontinuities, hotspots, and cold-spots in the irradiance profile.

As noted above, the flexible reflectors are flexible or semi-flexible. These flexible portions allow for non-damaging contact with plants and other objects and passively adapt to changing field conditions (i.e., by flexing away from the taller plants). This is important because some plants may change shape and size throughout the growing season. In some embodiments, the flexible reflectors on the front and back of the FDRSC device have a height that is shorter than the flexible reflectors on the sides of the FDRSC device-especially for FDRSC devices that will be moved over plants for field treatment. This enables the movement of the FDRSC device over rows of plants without damaging the plant canopies as the position of the plants are changed from outside the chamber of the FDRSC device to underneath or inside the chamber of the FDRSC device and, then again to the outside of the chamber as the FDRSC device moves to the next plant.

In one embodiment, the side flexible reflectors have a width that is approximately equal to the length of the array frame to which they are attached; a length that is from about 5 in. to about 30 in., e.g., 5 in., 6 in., 7 in., 8 in., 9 in., 10 in., 11 in., 12 in., 13 in., 14 in., 15 in., 16 in., 17 in., 18 in., 19 in., 20 in., 21 in., 22 in., 23 in., 24 in., 25 in., 26 in., 27 in., 28 in., 29 in., or 30 in.; and a thickness of about 0.1 mm to about 2 mm, e.g., 0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, or 2 mm. Preferably, the length and thickness of the side flexible reflectors is about 15 in. to about 25 in. and about 0.3 mm to about 1 mm, respectively. In one particular embodiment, the side flexible reflectors are about 15 in. to about 20 in. in length and about 0.5 mm thick. On the other hand, the front and back flexible reflectors tend to have a shorter length (about 25% to about 60% shorter) as compared to the side flexible reflectors. In general, the flexible reflectors will have a width approximately equal to the width of the array frame to which they are attached; a length that is from about 5 in. to about 25 in., e.g., 5 in., 6 in., 7 in., 8 in., 9 in., 10 in., 11 in., 12 in., 13 in., 14 in., 15 in., 16 in., 17 in., 18 in., 19 in., 20 in., 21 in., 22 in., 23 in., 24 in., or 25 in.; and a thickness of about 0.1 mm to about 2 mm, e.g., 0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, or 2 mm. Preferably, the length and thickness of the front/back flexible reflectors is about 8 in. to about 20 in. and about 0.3 mm to about 1 mm, respectively. In one particular embodiment, the front/back flexible reflectors are about 10 in. in length and about 0.5 mm thick. In other embodiments, the flexible reflectors are made from non-reflective material, but coated in a diffuse reflective material to a thickness of about 0.1 mm to about 2 mm.

Moreover, the flexible reflectors and the diffuse reflective material of the array frame are highly reflective of UV-C light and capable of achieving higher irradiance with fewer UV-C light sources, thus maximizing the UV-C dose applied to the plant surfaces. In particular, the flexible reflectors and/or the diffuse reflective material will be at least about 80% reflective, e.g., 80%, 81%, 82%, 83%, 84%, 85%, 86%, 87%, 88%, 89%, 90%, 91%, 92%, 93%, 94%, 95%, 96%, 97%, 98%, 99%, 99.5%, or more reflective of UV-C light. In preferred embodiments, the flexible reflectors and/or the diffuse reflective material are at least 90% reflective of UV-C light. In other embodiments, the flexible reflectors and/or the diffuse reflective material are at least 95% reflective of UV-C light, or at least 98% reflective of UV-C light.

An exemplary FDRSC is depicted in FIG. 1 and consists of an array frame 10 and a set of flexible reflectors 85, 90. As shown in FIGS. 1A and 1B, the array frame 10 includes a top surface 15 that is constructed from a white cellular PVC trim sheet 20 and a set of five white cellular PVC trim barriers 25. While the array frame of the FDRSC can be constructed to have any desirable dimensions, in this embodiment, the array frame 10 is about 40.25 in. (about 102.2 cm) long and about 32.77 in. (about 83.26 cm) wide. The PVC trim sheet 20 has a thickness of about 0.125 in. (about 0.318 cm) and forms approximate right angles at opposite ends, which angles are reinforced by a pair of aluminum T-bars 30. For support, a series of five 40.25 in.×0.75 in.×1.5 in. (about 102.2 cm×1.91 cm×3.81 cm) PVC trim barriers 25 are attached parallel to each other and at approximate equal distances apart to the bottom surface 47 of the PVC trim sheet 20 by screws 45 (or any suitable attachment means) as shown in FIG. 1B.

Figure 1B:
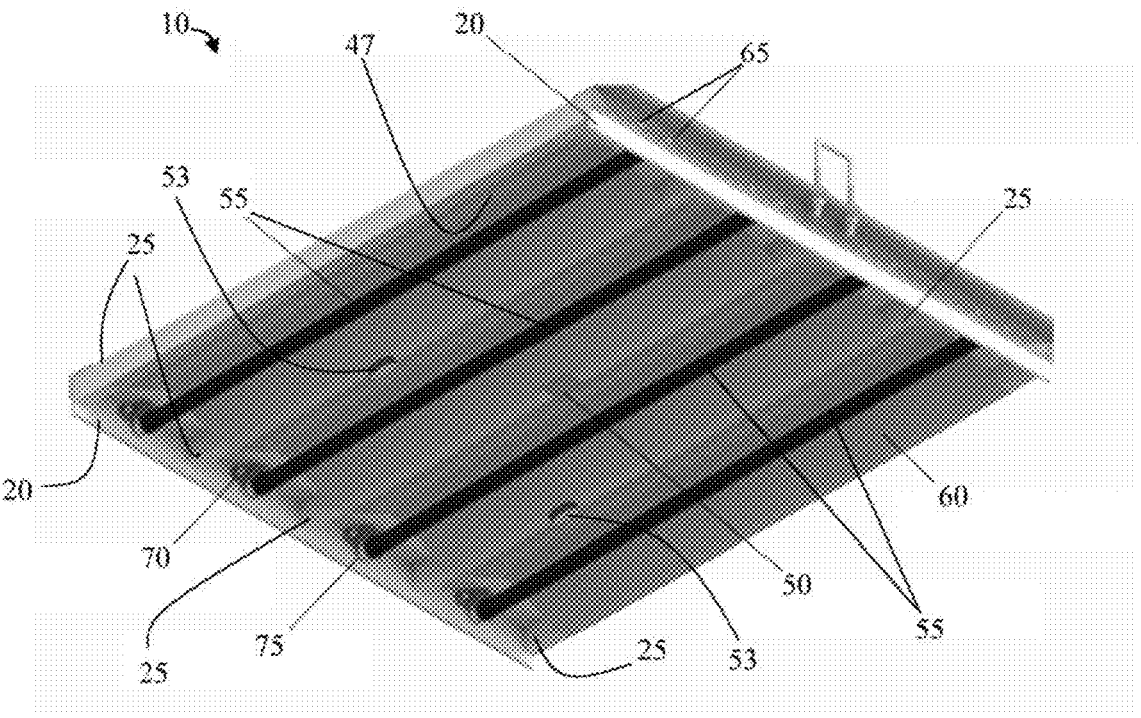
FIG. 1B is a bottom perspective view of an embodiment of the array frame of an exemplary FDRSC device.

Prior to installing the UV-C lamps, a diffuse light reflector 60 made from expanded PTFE (ePTFE) having a thickness of about 0.5 mm is draped over the bottom surface 47 of the PVC trim sheet 20 and attached to the PVC trim barriers 25 by an adhesive. In FIG. 1B, a series of four UV-C lamps 55 (G55T8 UVC 55W T8 UV Lamps, Light Spectrum Enterprises, Inc., Southampton, Pennsylvania, USA) are inserted into lamp holders 75, which are affixed to the sides of the PVC trim sheet 20 by way of the lamp holder mounts 70 and mounting screws 65. The UV-C lamps 55 are disposed over the diffuse light reflector 60 such that the diffuse light reflector 60 is underneath the UV-C lamps 55 and over the top of the PVC trim barriers 25 to produce angled sections 60' that taper toward either side (at approximately 25 degrees relative to the bottom surface 47) of each UV-C lamp 55 as best visualized in FIG. 1C.

Figure 1C:
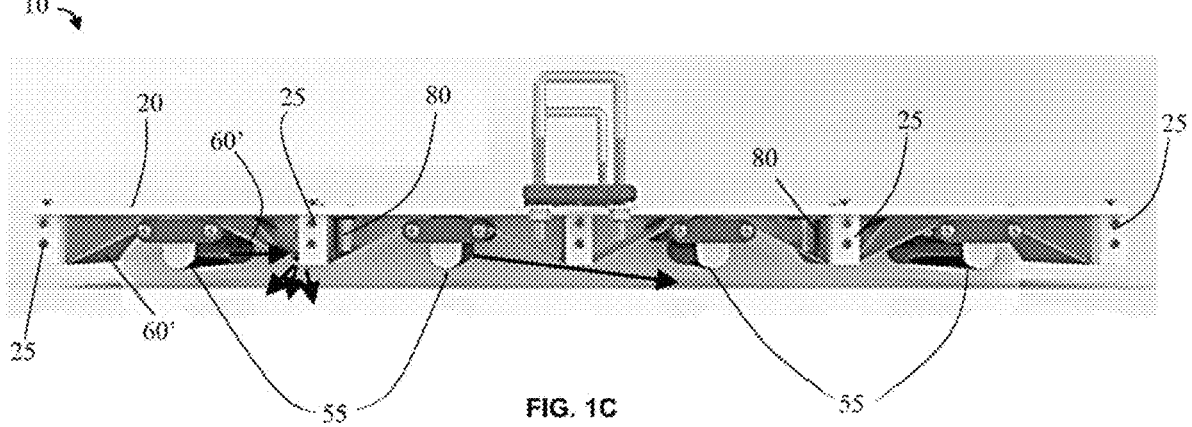
FIG. 1C is a cross sectional view of an embodiment of the array frame of an exemplary FDRSC device.

The UV-C lamps 55 are powered by 24 VDC batteries stepped down to 12 VDC and connected to a 120 VAC inverter and ballast (Fulman Workhorse 7 WH7-120-L). The ballasts are embedded into two of the PVC trim barriers 25 via the lamp ballast cutouts 80 as shown in FIG. 1C. In this particular embodiment, there are two ballasts, each of which are connected to two of the UV-C lamps 55. The UV-C lamps 55 emit light having a spectral wavelength of about 250 nm to about 255 nm. The angled sections of the ePTFE diffuse light reflector 60 deflects UV light emitted from the UV-C lamps downward and away from the neighboring UV-C lamp as shown by the arrows in FIG. 1C.

Figure 1D:
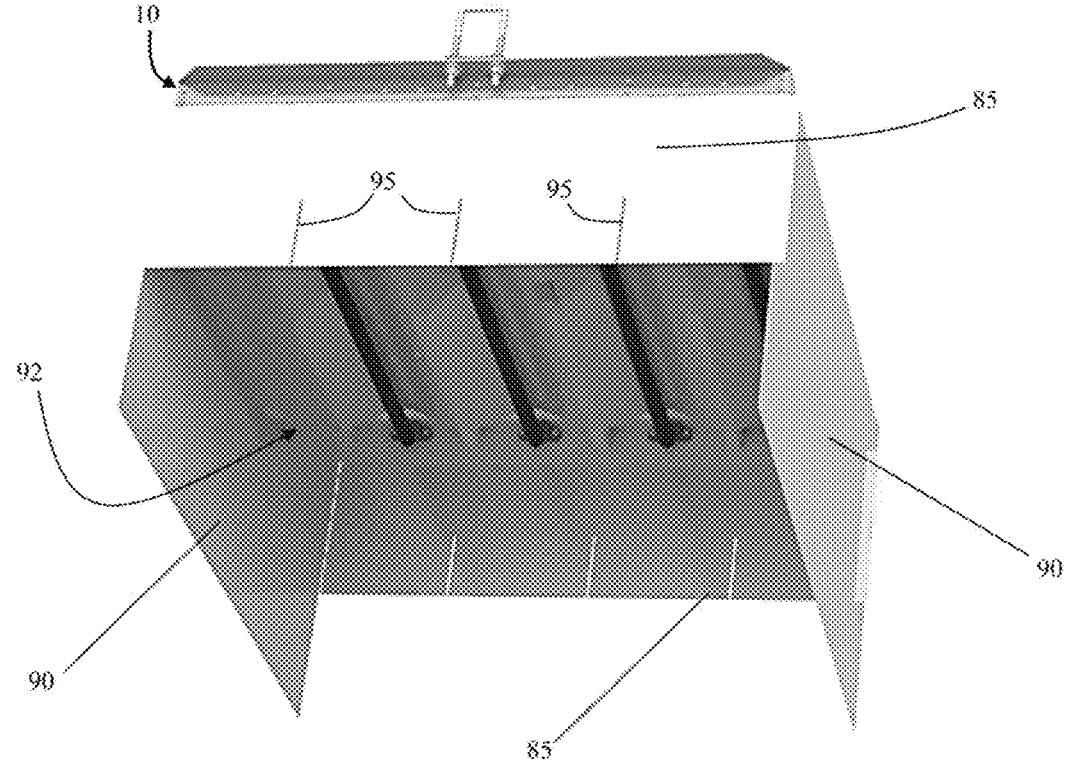
FIG. 1D is bottom perspective view of an exemplary FDRSC device.

To create a more uniform and diffuse light emission for treating plants and penetrating plant canopies, flexible reflectors are affixed to the array frame of the FDRSC device. As shown in FIG. 1D, four flexible reflectors 85, 90 are attached to the sides of the array frame 10, although other embodiments can have one or more open sides for receiving plants or when used in combination with an additional FDRSC device. In this particular embodiment, there are front and back flexible reflectors 85 attached to the bottom surface of the white cellular PVC trim sheet 20 sides, and two side flexible reflectors 90 attached to the bottom of the PVC trim barriers 25 on either end of the array frame 10 to form a chamber 92 in which plants can be treated. Each of the flexible reflectors 85, 90 are made from ePTFE. In this embodiment, the side flexible reflectors 90 have a greater height than the front and back flexible reflectors 85 to enable the movement of the FDRSC device across a row of plants without damaging the plants while providing the maximal amount of uniform diffuse UV-C light exposure. In this embodiment, the height of each side flexible reflectors 90 is about 19.75 in. (about 50.17 cm), while the height of the front and back flexible reflectors 85 is about 11.63 in. (29.54 cm). The front and back flexible reflectors 85 may also include multiple vertical cuts 95 for added flexibility to prevent damage to the plant canopies as the FDRSC moves across the plants during treatment. Further, the diffuse light reflective properties of the ePTFE flexible reflectors 85, 90 in combination with the diffuse light reflector 60 intensifies and uniformly distributes UV-C light emitted from the UV-C lamps 55 to create a UV-C light exposure chamber that penetrates plant canopies to enable increased efficiency and uniformity of the UV-C dosing as compared to existing technology.

The array frame 10 may also have one or more U-bolts 35 or other anchoring components for attachment of the FDRSC device to the ceiling or conveyor system in a greenhouse, a drone, or other type of autonomous mobile machine or robot for moving the FDRSC device across the plants to be treated. In FIG. 1C, the U-bolts 35 are attached to the aluminum T-bars 30 by flexible attachments 40.

The FDRSC devices described herein may include one or more detectors for measuring distances from the array frame and UV-C light sources to the surface of the ground or the surface(s) of the plant to which in-situ UV-C treatment is applied. The one or more distance detectors can be connected to a imaging program and used to calculate the distances between the UV-C light sources and the plant surfaces as explained further below. The distance detector can be, for example, any suitable imaging camera or range finder available in the art.

In addition to one or more distance detectors, the FDRSC device of the present disclosure may be equipped with one or more irradiance detectors or sensors. Alternatively, the irradiance detectors or sensors can be handheld by the user to take irradiance readings at particular points under the UV-C light sources. UV-C irradiance sensors are well known in the art and will include diodes sensitive to UV-light, and can convert the irradiance to a voltage output. The one or more irradiance detectors or sensors can be designed to collect irradiance data from many given points under the FDRSC device simultaneously, e.g., 2 to 300 points or more. For example, the UV-C light source(s) are configured to collect irradiance data on 10, 20, 30, 40, 50, 60, 70, 80, 90, 100, 110, 120, 130, 140, 150, 160, 170, 180, 190, 200, 210, 220, 230, 240, 250, 260, or more points. Alternatively, as explained below, the UV-C light source(s) can be configured to collect irradiance data on only a few or even one particular point under the array frame, which data can be used in combination with a dosing control calibration program to estimate the irradiance values for any other particular point under the array frame. This data can then be used by a software program, such as the software program described below in connection with the dosing control system, to determine the irradiance intensity and dosage at any particular point under the FDRSC. In a preferred embodiment, the irradiance detectors or sensors can be attached to the bottom surface of the FDRSC array frame.

The FDRSC device can be calibrated by creating an irradiance map where a separate UV-C sensor(s) (e.g., handheld device) are used to measure irradiance values at every point under the array, which values are compared to the values generated by the FDRSC UV-C sensors. Then, the UV-C sensor(s) can be used to collect irradiance data from a single point, or a few points, at a time. It being understood that, in embodiments were a single data point is measured by the UV-C detector at a time, the irradiance data at several points can be collected and used to predict the irradiance values under any other point under the FDRSC device.

To illustrate further, the irradiance values at these points can be compared to a larger collection of known measurements and used to interpolate between the measured points and then to extrapolate beyond these measurements to estimate irradiance values under any other point under the FDRSC device. For example, using a sensor to measure UV-C irradiance, one having ordinary skill in the art can collect a large set of measurements at many points under the FDRSC. A sensor is placed at a known point under at least one lamp in the array; preferably, under more than one lamp or under every lamp in the array. The user can then compare these sensor values (in real-time) to the measurements that were previously collected at the same point. The ratio between these points can then be applied to every point in the collected data, thus giving a true irradiance profile at every point under the FDRSC in real-time. For example, if the sensors under every lamp have an average reading of "5" at a given time. Then, if the previously collected data set showed at the time of collection that these same points showed an average value of "10", the skilled artisan can assume that at that instant, (because of various environmental factors) the irradiance values that are currently be measured in the field are exactly half of what was previously measured. This ratio is then applied to every point in the collected data set to determine the true irradiation values at every point under the FDRSC.

In the exemplary embodiments shown in FIG. 1, the FDRSC may include a distance detector 50 attached to the array frame 10. In this particular embodiment, the distance detector 50 is a DUO MLX stereo camera (Code Laboratories, Inc., Henderson, Nevada, USA). In addition, the array frame 10 includes two UV-C sensors 53 attached to the bottom surface 47. While this particular embodiment shows the UV-C sensors 53 attached to two barrier supports 25, any number of UV-C sensors can be attached the bottom surface 47 of the FDRSC device or attached to an accompanying autonomous vehicle or drone or even handheld by the user. In some embodiments, the UV-C sensor(s) are placed nearby and partially facing the UV-C light sources. In this manner, the UV-C sensor(s) can also be used to detect dead or malfunctioning UV-C light sources. In some embodiments, a single UV-C sensor can be used capable of detecting UV-C irradiance at multiple points under the FDRSC device.

In operation, the distance detector of the FDRSC device detects distances of objects below the array while the UV-C sensors detect irradiance at particular points under the array.

Both the distance detector 50 and the UV-C sensors 53 are in electronic communication with a central processing unit (CPU) located on-board the FDRSC device or external to the FDRSC device, e.g., on an autonomous land vehicle, drone, or mounting system. The signals captured by the distance detector 50 and the UV-C sensors 53 are interpreted by a dosing control system as explained in further detail below.

In one embodiment, the FDRSC device is attached to a conveyor belt, hydraulic arm, drone, or motorized vehicle for holding the FDRSC device over the plants to be treated. Moreover, the CPU, one or more UV-C sensors, and distance detectors can be mounted to the array frame of the FDRSC device or to the conveyor system, hydraulic arm, ceiling, stationary mount, or an autonomous vehicle or drone. For instance, in the embodiment discussed in detail below, one or more FDRSC devices are mounted to an autonomous vehicle, and while the UV-C sensors and distance detectors are mounted to the array frame, the CPU is on board the vehicle and both partly a component of the FDRSC's dosing control and partly a component of the autonomous vehicle's navigation system.

For stationary plant treatment, the FDRSC device can be programmed to switch on or off after a particular period of time to control the dosing. Thus, in one embodiment, the FDRSC device is attached to a ceiling or stationary arm that positions the FDRSC device over the plants to be treated. Once the desired dosing is achieved, the FDRSC device is turned off to prevent overexposure of the plants to UV-C irradiance.

On the other hand, for mobile field application, the dosing can be controlled by the speed of movement of the FDRSC device over the top of the plant to be treated. For instance, for field application, the FDRSC device is attached to an autonomous land vehicle or drone and moved across rows of plants at a desired speed, whereby the speed of the movement of the FDRSC device over a particular plant controls the dosing of that plant. In other words, the slower the movement of the FDRSC device over a particular plant, the longer that plant is exposed to the UV-C irradiance and, hence, the longer the period of time of the dosing. In other embodiments, the distance of the FDRSC device from the surface of the plants can be adjusted to change the dosing such that a greater distance provides a lower dosage while a lesser distance provides a higher dosage. Therefore, in an embodiment, the FDRSC is attached to a drone or an autonomous vehicle.

Dosing Control System

In one embodiment, the FDRSC device incorporates a dosing control system for measuring irradiance across the surface of a plant while providing a feedback loop that can adjust for the dosing amount and distance in real time. The dosing control system is in communication with at least one irradiance detector and at least one distance detector on the FDRSC device. In one embodiment, the dosing control system communicates with a stereo camera or digital range detector for measuring distance from the array frame to the surface/ground or plant canopy surface, and one or more UV-C sensors for measuring irradiance emitted from the UV-C light sources at any point(s) under the array frame. Stereo cameras and range detectors are available in the art, and selecting a suitable device for use with the FDRSC device is within the purview of the skilled artisan. Other suitable distance detectors include, but are not limited to, time-of-flight sensors, single scalar valued distance sensors, and the like. In a particular embodiment, the distance detector is a DUO MLX stereo camera (Code Laboratories, Inc., Henderson, Nevada, USA). The stereo camera compares offsets between two images and produces distance data comprising a matrix of grayscale image data as well as a matrix of measured distance. The stereo camera can be configured to capture many distance values at once or, alternative, can capture single distance point values at each point as it moves across a surface.

The UV-C sensor(s) can be an art-standard sensor and can be mounted on a plastic circuit board and attached to the bottom surface of the FDRSC array frame, e.g., adjacent to one or more, or each, UV-C light source. The UV-C sensor contains UV-C sensitive diodes that convert irradiance to a voltage output. The UV-C sensor is calibrated so that the voltage output is matched to voltage outputs from known UV-C values, it being understood that such calibration techniques are well within the purview of the skilled artisan. One or more UV-C sensors can be attached to the bottom surface of the array frame and can capture irradiance data for given points. In some embodiments, the UV-C sensor(s) collect irradiance data for each x, y, and z position treated by the UV-C light sources of the FDRSC device.

Both the distance detector and the UV-C sensor are connected to a computing device via electrical connections or wireless communication. The computing device includes a software program that executes the dosing control system program, which utilizes data from both the distance detector distance measurements and the UV-C sensor irradiance values to produce a predicted irradiance at any point under the FDRSC device.

The dosing control system program can be run on any suitable computing device available in the art, such as a desktop, laptop, mobile device, etc. The human user of the dosing control system program can input desired dosing parameters and visualize the dosing data in the form of heatmaps and irradiance profiles using a standard graphic user interface and display screen. The operation of standard computing devices and the hardware thereof is well within the purview of the skilled artisan and will not be described in further detail herein. In some embodiments, the dosing control program is run on an on-board central processing unit (CPU) incorporated into the FDRSC device or an autonomous vehicle on which the FDRSC device is mounted.

To calibrate the dosing control system, the user first creates a volumetric irradiance map (VIM). The VIM is created by positioning a UV-C sensing device at a number of points on a grid in the treatable range of the FDRSC device. At every point, the position (x(m), y(m), z(m)) of the sensor is recorded along with the irradiance (W/m²) relative to a fixed point on FDRSC. The values measured by the UV-C sensor(s) attached to the FDRSC are also recorded. Once these four-dimensional data points are collected, one fixed UV-C sensor on the FDRSC device is selected as the reference measurement. For each position, the linear relationship is determined between the reference measurement and the irradiance value measured at that position according to:

$$A = s(x, y, z)B(x, y, z) \qquad \text{[Equation 1]}$$

Where A is a sensor that is attached to the FDRSC and (x, y, z) and represents a specific point irradiated by the array in a coordinate system relative to the FDRSC. Prior to generation of the VIM, the calibration values at (x, y, z) are unknown. For every point (x, y, z), irradiance A and B are measured to determine the static(s) mapping value of s(x, y, z). The calibration process proceeds as another measurement B(x, y, z) is taken at a new position. Since A has already been determined, static mapping value s(x, y, z) can be calculated from the new B(x, y, z) value. Once multiple measurements have been taken, a set of s(x, y, z) values will be obtained. This set of values is finite and discrete depending on the number of measurements taken, so one having ordinary skill in the art can interpolate between them and extrapolate beyond them to estimate s(x, y, z) in finer resolution. The VIM calibration map allows the user to take the FDRSC device to the field, which includes the UV-C sensor that obtained the value for A. Thus, for any x, y, z position away from the array, the user can retrieve a value s(x, y, z) and solve for equation 2:

$$B(x, y, z) = A/s(x, y, z) \qquad \text{[Equation 2]}$$

The VIM is a functional mapping from the reference measurement such that for any new reference measurement, the value of any other measured position can be found through linear transformation. The accuracy of this estimation is dependent on the number of points measured as well as the average distance between points. To achieve the best estimation, the user must take many points of data at consistent distance intervals over the entire treatable area of the FDRSC array.

Figure 2A:
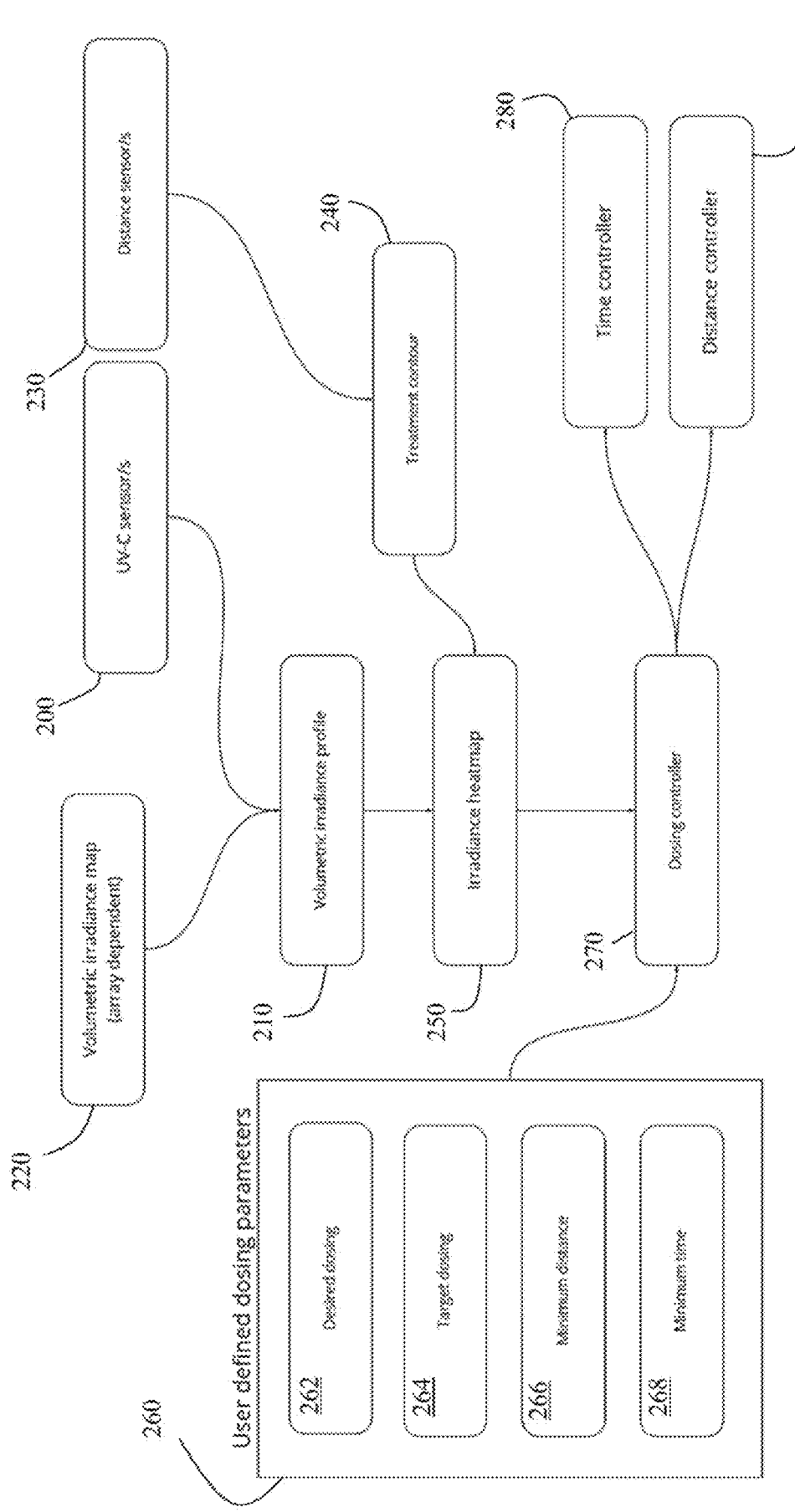
FIG. 2A depicts a flow diagram of the dosing control system.
Figure 2B:
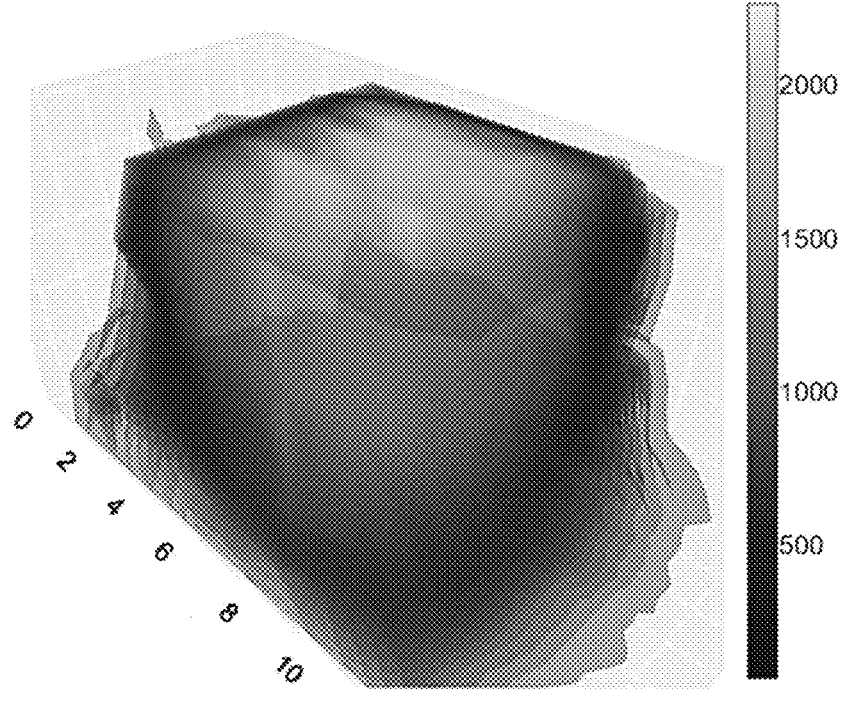
FIG. 2B is an exemplary Volumetric Irradiance Profile. The lighter colors indicate higher intensity irradiance.

A flowchart of the dosing control system is shown in FIG. 2A. The UV-C sensors 200 capable of measuring irradiance emitted from the UV-C light sources having a spectral wavelength between about 100 nm to about 280 nm are attached to the bottom surface of the array frame in close proximity to each UV-C light source. The UV-C sensors convert UV-C irradiance emitted by the light sources to electrical signals that are sent to the computing device. The dosing control system uses the VIM 220 as one of the inputs. The static mapping values s(x, y, z) allow for determining irradiance value B(x, y, z) given the measured irradiance value A. The volumetric irradiance profile 210 are the irradiance values at any (x, y, z) point around the array. This is the solution B for every point in proximity of the array. An example of a volumetric irradiance profile is shown in FIG. 2B.

The distance detector/sensor(s) 230 measure distances from one or more points of reference to the surfaces treated by the FDRSC device and generates a treatment contour 240 of surfaces near the array, which are at particular (x, y, z) positions. This treatment contour 240 data is combined with the mapping data from the volumetric irradiance profile 210 to create an irradiance heatmap 250. The irradiance heatmap 250 is the subset of irradiance values from the volumetric irradiance profile 210 that fall on the (x, y, z) positions determined by the treatment contour 240. In other words, the distances in the treatment contour 240 are used to search for irradiance values in the volumetric irradiance profile 210.

The user is enabled to input user-defined dosing parameters 260, including desired dosing 262, target dosing 264, minimum distance 266, and minimum time 268. The desired dosing 262 is defined as a scalar dosing value that is ideal dosing to kill a particular pest or pathogen. The target dosing 264 is selected from a range of dosing values between adequate dosing and the plant damage threshold. The minimum distance 266 is the minimum distance the FDRSC device can be placed from the treatment surfaces. Finally, the minimum time 268 is the minimum amount of time that the FDRSC device can irradiate a treatment surface. These user-defined dosing parameters 260 are utilized by the dosing controller 270 subroutine to determine dosing under variable time and distance scenarios (e.g., utilizing a monte Carlo style simulation or a defined optimization criterion configured to analytically solve for the best height and/or time) to determine the combination of height and time that either achieves the desired dosing or, if in achieving the desired dosing there are surfaces outside the target dosing, find the nearest combination of height and time that keeps most surfaces in the target dosing. Values of distance and time are bounded by hardware constraints and/or software minimums on distance and time. Depending on hardware or user preference, values for either distance or time can be static allowing for only one controllable variable. The optimization minimizes treatment time to emphasize efficiency.

The dosing controller 270 subroutine uses data from the irradiance heatmap 250, volumetric irradiance profile 210, and user-defined dosing parameters 260 to determine a treatment distance and time. The dosing controller 270 data is then sent to the time controller 280 subroutine to adjust the amount of time the FDRSC provides irradiance to surface/s and track elapsed time (i.e. controls a switch or the speed the array passes over treatment surfaces, depending on the system). For instance, the time controller 280 sends electrical signals to a drone, autonomous robot or other mobile vehicle, or conveyor system to speed up or slowdown movement of the FDRSC device, which, in turn, decreases or increases, respectively, the UV-C dosing on a given surface. The dosing controller 270 data can also be sent to the distance controller 290 subroutine to adjust the distance between the FDRSC device and the treatment surfaces. The distance controller 290 subroutine then sends electrical signals to the drone, autonomous robot or other mobile device, or conveyor system to adjust the height of the FDRSC device relative to the treatment surface. The speed and distance control is explained in additional detail below.

Thus, the dosing control system incorporates a feedback loop to ensure accurate target dosing of plant canopies without exceeding the plant damage threshold. Therefore, the dosing control system optimizes in-situ treatment of plants by achieving efficient and adequate UV-C dosing of plants to reduce or eradicate pests and pathogens.

Real-Time Dosing Control of the FDRSC Device

Figure 3:
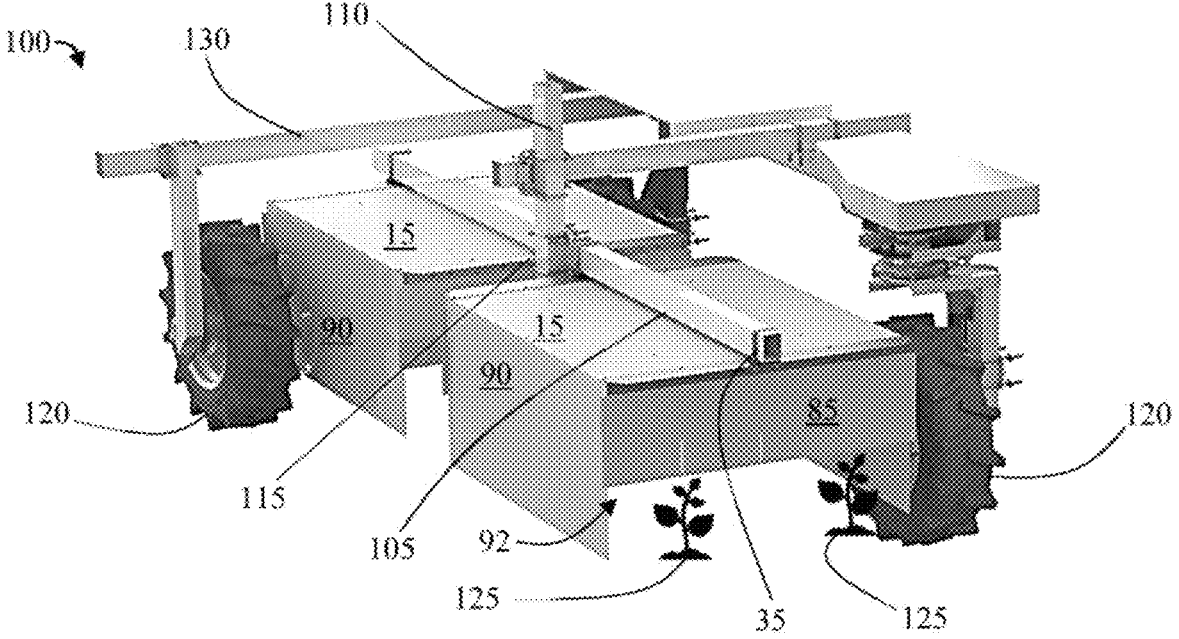
FIG. 3 is a front perspective view of an exemplary autonomous vehicle and pair of FDRSC devices.

The dosing control system can be employed with an autonomous vehicle or drone to adjust the movement of the autonomous vehicle or drone to control the UV-C dosage applied to the plants. FIG. 3 depicts an example of an FDRSC device attached to an autonomous vehicle or robot. The autonomous vehicle 100 may consist of a frame 125 that connects three wheels 120, at least one of which are connected to a wheel motor controlled by a motor controller, it being understood that two or all three wheels can be connected to a wheel motor and motor controller. The wheel motor may be a brushed 24 VDC motor and may be connected to an encoder and a worm drive gearbox. The motor controller can be any suitable art-standard motor controller, such as the RoboClaw 2x30A Motor Controller (BasicMicro Motion Control, Temecula, CA 92592, USA). The autonomous vehicle also comprises a battery and an on-board central processing unit (CPU).

As shown in FIG. 3, the autonomous vehicle 100 includes a vertical arm 110 to which is attached a lateral support or bar 105. In this embodiment, there are two FDRSC devices attached to the lateral support bar 105 by the U-bolts 35 of the array frames 100 (see FIG. 1A). The CPU of the autonomous vehicle 100 may be programmed to move the vehicle across a field according to the pre-programmed speed. Alternatively, the speed of the autonomous vehicle 100 can be controlled by a separate computing device that communicates with the vehicle's CPU via a wireless network. The signals from the on-board CPU control the speed of the autonomous vehicle 100 by communicating with a motor controller component, which in turn moves the drive motor and steering motor. The on-board CPU defines the steering angle and drive wheel velocity by computing the desired number of encoder counts needed to move the autonomous vehicle at a desired speed along a desired path. The motor controller senses rotation of the smart vehicle motors connected to the wheels 120 by measuring encoder counts. Using an onboard PID controller, the motor controller drives these encoder counts to those communicated by the CPU over a serial connection. If the autonomous vehicle encounters a hill, for example, its motor controller automatically increases the draw from the battery to maintain the desired wheel speed. In some embodiments, the CPU sends a constant desired speed to the motor controller and naively treats the field with no knowledge of actual dosing. In another embodiment, the speed of the autonomous vehicle 100 is controlled by the dosing control system described above. As the dosing control system suggests changes in speed and communicates to the on-board CPU of the autonomous vehicle to update the speed input, which then sends a signal to the motor controller to adjust the speed of rotation of the wheels 120.

As the autonomous vehicle 100 moves across the field, the FDRSC devices are moved over the tops of the plants 125. As each FDRSC device moves over a plant 125, the UV-C light sources 55 on the bottom surface of the array frame 10 emit UV-C irradiance (see FIG. 1B) thereby treating the plant surfaces. The speed of the autonomous vehicle's movement controls the dose of UV-C irradiance to which the plant is exposed—the slower the speed, the higher the UV-C dose and vice versa.

The FDRSC devices can be positioned manually along the length of the lateral support bar 105 to adjust the spacing between the devices. Further, the vertical height of the FDRSC devices can be adjusted in relation to the plant or ground surface by raising or lowering the vertical arm 110. These adjustments can be done manually or by way of automation. For instance, in one embodiment, the vertical arm 110 includes a motor, such as a stepper motor, and an encoder, such as a rotary encoder, for receiving electrical signals from the on-board CPU to raise or lower the lateral support bar 105 and FDRSC devices accordingly and in response to program instructions from the dosing control system. For instance, the distance controller subroutine receives input on the current distance setting of the FDRSC device and also receives input from the dosing controller, which determines or predicts the optimal height for applying the irradiance dosing to the plants. The dosing controller then signals the distance controller to increase or decrease the distance and, in turn, the distance controller communicates with the motor of the vertical arm 110. Alternatively, the vertical arm 110 is replaced with a motorized scissor jack. For manual adjustment, the FDRSC devices can be raised or lowered by manually adjusting the U-bolts 35 or the vertical arm 110.

The operation of the autonomous vehicle 100 can be controlled by the dosing control system described above. In this manner, the distance detector 50 and the UV-C sensor(s) 53 of the array frame 10 are connected to and communicate with the onboard autonomous vehicle 100 CPU. The CPU includes a software program that utilizes data from both the distance detector 50 distance measurements and the UV-C sensor(s) 53 irradiance values to produce a predicted irradiance dosage at any point under the FDRSC device. As explained above, the feedback loop causes the time controller 280 and/or the distance controller 290 subroutines to send electrical signals to the autonomous vehicle 100 to control the speed and height of the FDRSC devices, respectively. In some embodiments, the dosing control system and its subroutines are run on a computing device or CPU incorporated into the FDRSC. In other embodiments, the dosing control system and its subroutines are run on a computing device or CPU on-board the autonomous vehicle or other mounting system.

For instance, if the imaging sensor 50 observes taller plants at the front of the array frame 10, then the dosing controller 270 may determine that a decrease in treatment time is needed—otherwise the taller plants will get too much dosing. This decreased treatment time data will be sent to the time controller 280. In this particular embodiment, the time controller 280 signals the motor controller to adjust the speed of the autonomous vehicle 100 by adjusting the rotation of the wheels 120 via the wheel motor. A faster speed reduces treatment time as the FDRSC moves to the next plant in a shorter period of time, so the dosing controller 270 will determine that a faster speed is required, and the time controller 280 will send a signal to the motor controller, which physically adjusts the speed of the wheels 120 in real time. For example, if the dosing control system determines that a 6 J/m$^2$ dosing is desired, and the irradiance heatmap shows an irradiance of 1 W/m$^2$, then the dosing controller would suggest a 6 second treatment time to the time controller. If the FDRSC is, for example, 36 inches long, then the time controller would select a speed of 6 in/s and instruct the motor controller to achieve a 6 second treatment time.

In another embodiment, the autonomous vehicle 100 may have had a motor driver that is not controllable in real time, meaning the autonomous vehicle 100 can only travel at a single speed. As such, the dosing controller 270 will adjust the dosing by changing the dosing distance (or the UV-C light source irradiance). Thus, rather than send a signal to the time controller 280 for controlling the vehicle speed, the dosing controller 270 will cause the distance controller 290 to send a signal to the encoder of the vertical arm 110 or, alternatively, a motorized scissor jack to raise or lower the lateral support bar 105 and, subsequently adjust the distance between the FDRSC and the surface of the plant. Greater distance provides less dosage, while shorter distance provides greater dosage. In addition, the dosing controller 270 can cause the distance controller 290 to raise and lower the vertical arm 110 if the imaging sensor 50 data indicates taller or shorter plants. Furthermore, the speed and height of a drone or other flying device can be controlled in a similar manner as will be understood by the skilled artisan in view of the present disclosure.

If manual height adjustment is desired, or if the autonomous vehicle is not adapted for automated adjustment of the FDRSC devices, the user can log into a computing device to visualize the FDRSC height adjustment feedback, which may indicate to the user that the FDRSC's height should be adjusted in order to achieve the most consistent average distance between the array frame and the surfaces of the plants. For instance, if the bottom surface of the array frame is 10 inches from the plant canopies, but the optimal average distance from the array frame to the plants as predicted by the dosing control system is 12 inches, then the user will learn that he or she should manually adjust the height by extending the vertical arm or the U-bolts by 2 inches.

Alternatively, the FDRSC devices may be held into place by a stationary arm or similar support. In such an embodiment, the UV-C dosage applied to the plants cannot be adjusted in real time by raising or lowering the FDRSC device or changing the speed at which the FDRSC device is moved over the plants. Thus, in this embodiment, UV-C light source power supply may be controlled by a CPU (either incorporated to the array frame or external to the array frame), and the dosing controller 270 will send electrical signals to the power source to turn off the UV-C dosage after the desired dosing time.

In-Situ Treatment of Plants Using the FDRSC Device

The FDRSC devices described above can be used to apply UV-C irradiance to plants to reduce or eradicate pests or pathogens infesting the plants. The FDRSC device design provides for uniform, efficient, and adequate UV-C dosage coverage of plant canopies without damaging the plants or requiring a large power source.

To illustrate further, naive in-situ treatment of plants with UV-C can damage the plants if dosing is too high. On the other hand, a UV-C irradiance dosage that is too low will not effectively reduce or eradicate pets or pathogens on the plant. The FDRSC device of the present disclosure creates a chamber of uniform UV-C irradiance to ensure that the entire plant canopy receives sufficient coverage and adequate UV-C dosing. This is achieved due to the diffusion properties of the array frame and flexible reflectors. In addition, the dosing control system incorporates a feedback monitoring aspect that adjusts the UV-C dosing to prevent exceeding the plant damage threshold and ensure optimal and adequate dosing. Moreover, the dosing control system allows for user inputs of desired dosing parameters as the UV-C dosing required for treatment of different pests or pathogens may require different target doses.

Furthermore, UV-C target doses may vary by plant. For instance, blueberry plants span a larger distance requiring a larger range of distances that need to be treated. As such, increased dosing may be required for in-situ treatment to ensure adequate dosing to all areas of the blueberry plant as compared to plants with smaller plant canopies. Strawberry plants tend to have denser plant canopies as compared to other plants. The denser canopies include plant parts that are partially shaded during treatment therefore requiring higher levels of UV-C dosing to ensure adequate coverage. Depending on the plant surfaces detected by the dosing control system, the FDRSC device can be automatically adjusted in terms of treatment time or distance to achieve the target dose. As described above, the dosing control system enables real-time adjustment of UV-C dosing.

The FDRSC devices of the present invention also provide greater UV-C efficiency as the diffuse light-reflecting properties of the array frame and flexible reflectors provide passive and non-power-consuming UV-C irradiance sources by redirecting UV-C irradiance that would otherwise not contact the plant surfaces. The reflection chamber of the FDRSC device maximizes the effectiveness of the UV-C light sources by scattering the light to many plant surfaces and by effectively surrounding the plants in UV-C light as compared to devices with non-diffuse or non-reflective surfaces. What is more, UV-C treatment devices with specular arrays do not produce uniform irradiance and tend to apply UV-C irradiance unevenly throughout a plant canopy, which can cause damage to some surfaces of the plant while surfaces deep within the plant canopy receive inadequate UV-C dosage allowing the pests or pathogens to survive and spread to and re-infest other parts of the plant.

Additionally, the dosing control system enables real-time adjustments to plant dosing thereby ensuring adequate dosing to plants having canopies of different sizes, densities, and complexities, which can change over time and in response to changing environments. For instance, it can be difficult to treat plants on farms due to difficulty in penetrating certain plant canopies and treating the undersides of leaves. Moreover, there are environmental factors that change across the landscape and over time that impact the irradiance received by the plants, the target dosage needed to effectively treat the plants, the distance between the plant surfaces and the array frame, and the available space in which to operate. Thus, the flexible and diffuse FDRSC chamber provides efficient and uniform UV-C irradiance that can be moved across the plant landscape without damaging the leaves and stalks of the plants, is not impacting by rain or wind, and can be adjusted by the dosing control system in real time thereby providing a dynamic and effective pest control system without exceeding the plant damage threshold or requiring hazardous chemical treatments. For instance, other systems may require placement of UV-C lamps on the side of the frame to ensure adequate dosing to the underside of leaves. However, this would require rigid side frames that would damage crops as the device is moved across the field. Finally, the passive-light amplification properties of the FDRSC chamber allows for more efficient dosing without requiring many UV-C light sources, which would require additional power sources. Thus, the FDRSC device of the instant invention can be moved across large fields using a battery powered autonomous vehicle or drone.

The devices described herein can be used to treat any plant or crop that is infested by pests or pathogens including, but not limited to, asparagus, barley, beans, beets, blueberries, broccoli, cabbage, canola, cauliflower, celery, cranberries, corn, cotton, feed grains, flowers, garlic, grapes, lentils, lettuce, mushrooms, oats, peanuts, peas, peppers, potatoes, pumpkins, rice, sorghum, soybeans, spinach, squash, strawberries, sugar cane, sweet potatoes, tobacco, tomatoes, turnips, watermelon, wheat, and the like. The FDRSC device can be used to reduce or eradicate pests or pathogens on plants including, but not limited to, fungi (e.g., mildew), bacteria, insects (e.g., spider mites), mollicutes, viruses, protozoa, viroids, and other parasitic organisms. The presence of plant infection or infestation by pests or pathogens can be observable by one having ordinary skill in the art of plant biology or farming. Thus, the skilled artisan can observe certain parameters of plant infection, such as leaf rust, stem rust, sclerotinia, spots, damping, chlorosis, lesions, bacterial oozing, fruit rust, cankers, crown galls, Sheperd's crook stem ends, mosaic leaf patters, crinkled leaves, yellowed leaves, plant stunting, mycelium growth, mold growth, fruiting bodies, bacterial odors, stem rot, blight, fungal rings, water soaking, bacterial streaming, stunted growth, wilting, and the like. After treatment, the resolution of these symptoms (i.e., the decrease or absence of these parameters) are indicative of effective in-situ UV-C treatment. In one embodiment, the pests or pathogens on a plant are reduced by at least 5%, e.g., 5%, 10%, 15%, 20%, 25%, 30%, 35%, 40%, 45%, 50%, 55%, 60%, 65%, 70%, 75%, 80%, 85%, 90%, 95%, 97%, 99%, 99.9% or more following in-situ UV-C light treatment using the present FDRSC device as compared to the plant prior to in-situ treatment with UV-C light. In a preferred embodiment, the pests or pathogens are reduced by at least 10% following in-situ UV-C treatment; more preferably, the pests or pathogen are reduced by at least 25%. In some embodiments, it can take up to several days or more following in-situ treatment for certain pests or pathogens to be reduced or eradicated since the UV-C irradiance does not kill the pests or pathogens immediately, but rather reduces or eliminates their capability of reproducing. In such a case, the normal life-cycle of the pests or pathogens is complete, but the infestation or infection is eliminated due to the lack of offspring.

Furthermore, it may be desired to treat plants with UV-C light to eradicate or significantly reduce pest or pathogen infestation prior to the onset of observable parameters, or for preventative measures. Therefore, a suitable method of treatment may include identifying or providing the plants to be treated and subjecting the plants to UV-C irradiance at a desired dose and treatment time. For visibly infected plants, the parameters of plant infestation or infection will tend to be observable by the practitioner. Thus, the method may include the steps of identifying or providing the plants in need of UV-C treatment or for which UV-C treatment is desired, subjecting the plants to the UV-C irradiance at a desired dose and for a desired treatment time, and then measuring (e.g., observing) one or more parameters of plant infection. The measuring of the parameters can be done prior to, during, and/or after the treatment. It being understood that the disappearance or lessening of the parameters is indicative of effective treatment (i.e., a decrease or eradication of the pest or pathogen).

The UV-C treatment will include emittance of light having a spectral wavelength in the ultraviolet range, i.e., between about 10 nm to about 400 nm. In a preferred embodiment, the UV light is UV-C light having a spectral wavelength of about 100 nm to about 280 nm. In a particular embodiment, the UV-C light has a spectral wavelength of about 220 nm to about 230 nm, or about 250 nm to about 260 nm. The desired dose can be selected by the user of the device and may range from about 0.5 $J/m^2$ to about 20 $J/m^2$, e.g., 0.5 $J/m^2$, 0.6 $J/m^2$, 0.7 $J/m^2$, 0.8 $J/m^2$, 0.9 $J/m^2$, 1 $J/m^2$ to about 20 $J/m^2$, e.g., 1 $J/m^2$, 2 $J/m^2$, 3 $J/m^2$, 4 $J/m^2$, 5 $J/m^2$, 6 $J/m^2$, 7 $J/m^2$, 8 $J/m^2$, 9 $J/m^2$, 10 $J/m^2$, 11 $J/m^2$, 12 $J/m^2$, 13 $J/m^2$, 14 $J/m^2$, 15 $J/m^2$, 16 $J/m^2$, 17 $J/m^2$, 18 $J/m^2$, 19 $J/m^2$, 20 $J/m^2$, 21 $J/m^2$, 22 $J/m^2$, 23 $J/m^2$, 24 $J/m^2$, 25 $J/m^2$, 26 $J/m^2$, 27 $J/m^2$, 28 $J/m^2$, 29 $J/m^2$, or 30 $J/m^2$, depending on the area and density of the plant canopy. In a particular embodiment, the desired UV-C dose is from about 1 $J/m^2$ to about 10 $J/m^2$. For larger and denser plant canopies, the desired target dose is in the range from about 1 $J/m^2$ to about 1,200 $J/m^2$, e.g., 1 $J/m^2$, 10 $J/m^2$, 20 $J/m^2$, 30 $J/m^2$, 40 $J/m^2$, 50 $J/m^2$, 60 $J/m^2$, 70 $J/m^2$, 80 $J/m^2$, 90 $J/m^2$, 100 $J/m^2$, 200 $J/m^2$, 300 $J/m^2$, 400 $J/m^2$, 500 $J/m^2$, 600 $J/m^2$, 700 $J/m^2$, 800 $J/m^2$, 900 $J/m^2$, 1,000 $J/m^2$, 1,200 $J/m^2$, or 1,200 $J/m^2$. Preferably, the target dose is less than about 1,200 $J/m^2$; more preferably, it is less than about 750 $J/m^2$. For instance, the target dose for plants with dense plant canopies, such as strawberries, may be in the range from about 60 $J/m^2$ to about 750 $J/m^2$; preferably from about 60 $J/m^2$ to about 250 $J/m^2$. In a particular embodiment, plants with very dense canopies, such as strawberries, are treated with a desired dose of about 240 $J/m^2$. In another embodiment, the desired target dose is at least about 0.5 $J/m^2$, e.g., 0.5 $J/m^2$, 0.6 $J/m^2$, 0.7 $J/m^2$, 0.8 $J/m^2$, 0.9 $J/m^2$, 1 $J/m^2$, 2 $J/m^2$, 3 $J/m^2$, 4 $J/m^2$, 5 $J/m^2$, 6 $J/m^2$, 7 $J/m^2$, 8 $J/m^2$, 9 $J/m^2$, 10 $J/m^2$, 11 $J/m^2$, 12 $J/m^2$, 13 $J/m^2$, 14 $J/m^2$, 15 $J/m^2$, 16 $J/m^2$, 17 $J/m^2$, 18 $J/m^2$, 19 $J/m^2$, 20 $J/m^2$, 30 $J/m^2$, 40 $J/m^2$, 50 $J/m^2$, 60 $J/m^2$, or more. For instance, in one exemplary embodiment, the target dose can be at least about 1 $J/m^2$, or at least about 5 $J/m^2$.

The period of time the plants are subjected to the UV-C dose may be at least 1 second, e.g., 1 sec, 2 sec, 3 sec, 4 sec, 5 sec, 6 sec, 7 sec, 8 sec, 9 sec, 10 sec, 11 sec, 12 sec, 13 sec, 14 sec, 15 sec, 16 sec, 17 sec, 18 sec, 19 sec, 20 sec, 21 sec, 22 sec, 23 sec, 24 sec, 25 sec, 26 sec, 27 sec, 28 sec, 29 sec, 30 sec, 35 sec, 40 sec, 45 sec, 50 sec, 55 sec, 60 sec, 2 min, 3 min, 4 min, 5 min, or more depending on the area and density of the plant canopy. In another embodiment, the period of time to achieve adequate dosing of the plant or plant part is less than about 5 minutes; preferably, less than about 3 minutes; more preferably, less than about 60 seconds. In another embodiment, the dosing of the plant is from about 15 sec to about 30 sec. In a preferred embodiment, the dosing of the plant is for at least 3 sec; more preferably, at least 5 sec. In some embodiments, the period of time to achieve adequate dosing of the plant or plant part is between about 3 sec and about 10 sec; preferably, between about 1 sec and about 5 sec. It being understood that the target dosing is achieved by a combination of UV-C light emission intensity and time of exposure. Additionally, a plant exhibiting observable parameters or signs of pest or pathogen may require longer treatment times or dosages as compared to plants of the same type that do not exhibit the observable parameters or signs of pest or pathogen infection/infestation.

For mobile UV-C treatment methods, the FDRSC device can be attached to an autonomous vehicle or robot or a drone as discussed above. Therefore, the target dose can be achieved by selecting a particular speed of the autonomous vehicle or robot or a drone as it moves over the plants to be treated for any given UV-C emission. For instance, the selected speed can be anywhere from about 1 in./s to about 120 in./s, or more, e.g., 1 in./s, 2 in./s, 3 in./s, 4 in./s, 5 in./s, 6 in./s, 7 in./s, 8 in./s, 9 in./s, 10 in./s, 11 in./s, 12 in./s, 13 in./s, 14 in./s, 15 in./s, 16 in./s, 17 in./s, 18 in./s, 19 in./s, 20 in./s, 21 in./s, 22 in./s, 23 in./s, 24 in./s, 25 in./s, 26 in./s, 27 in./s, 28 in./s, 29 in./s, 30 in./s, 35 in./s, 40 in./s, 45 in./s, 50 in./s, 55 in./s, 60 in./s, 65 in./s, 70 in./s, 75 in./s, 80 in./s, 85 in./s, 90 in./s, 95 in./s, 100 in./s, 105 in./s, 110 in./s, 115 in./s, 120 in./s, or more. Again, the adequate or target dosage will be determined by the user depending on the particular plant to be treated and the particular pest or pathogen to be eradicated, and such determination will be within the purview of the skilled artisan given the present disclosure. Moreover, the particular dosage can be adjusted in real time by the dosing control system as discussed above.

The UV-C treatment can be performed at least once a day, every other day, once per week, every other week, or once per month as desired. The treatment duration can be for about 1 day to many months depending on the plant or infestation. For instance, in one embodiment, the treatment is performed every other day for a period of at least about 1 week.

In another embodiment, the UV-C treatments are applied to the plants at night to avoid UV-C damage to plants that are already subject to the solar rays from the sun. The treatments are then followed by a dark period to prevent activation of the light-activated DNA repair mechanism of certain pathogens. For instance, the UV-C treatment can be performed every other night.

REFERENCE NUMBERS

10—Array frame
15—Top surface of array frame
20—PVC trim sheet
25—PVC trim barrier
30—Aluminum T-bar
35—U-bolt attachment
40—Flexible spacer
45—Screws (for attaching trim barriers to trim sheet)

47—Bottom surface of array frame
50—Distance detector
53—UV-C sensor
55—UV-C lamps
60—Diffuse light reflector (ePTFE)
65—Lamp mounting screws
70—Lamp holder mount
75—Lamp holder
80—Lamp ballast cutout (containing ballast)
85—Front and Back flexible reflectors (ePTFE)
90—Side flexible reflectors (ePTFE)
92—chamber
95—Vertical cuts
100—autonomous vehicle
105—lateral support
110—vertical arm
115—adjustable mount
120—wheel
125—plant
130—frame The following examples are provided to describe the invention in greater detail. They are intended to illustrate, not to limit, the invention.

Example 1

Figure 4:
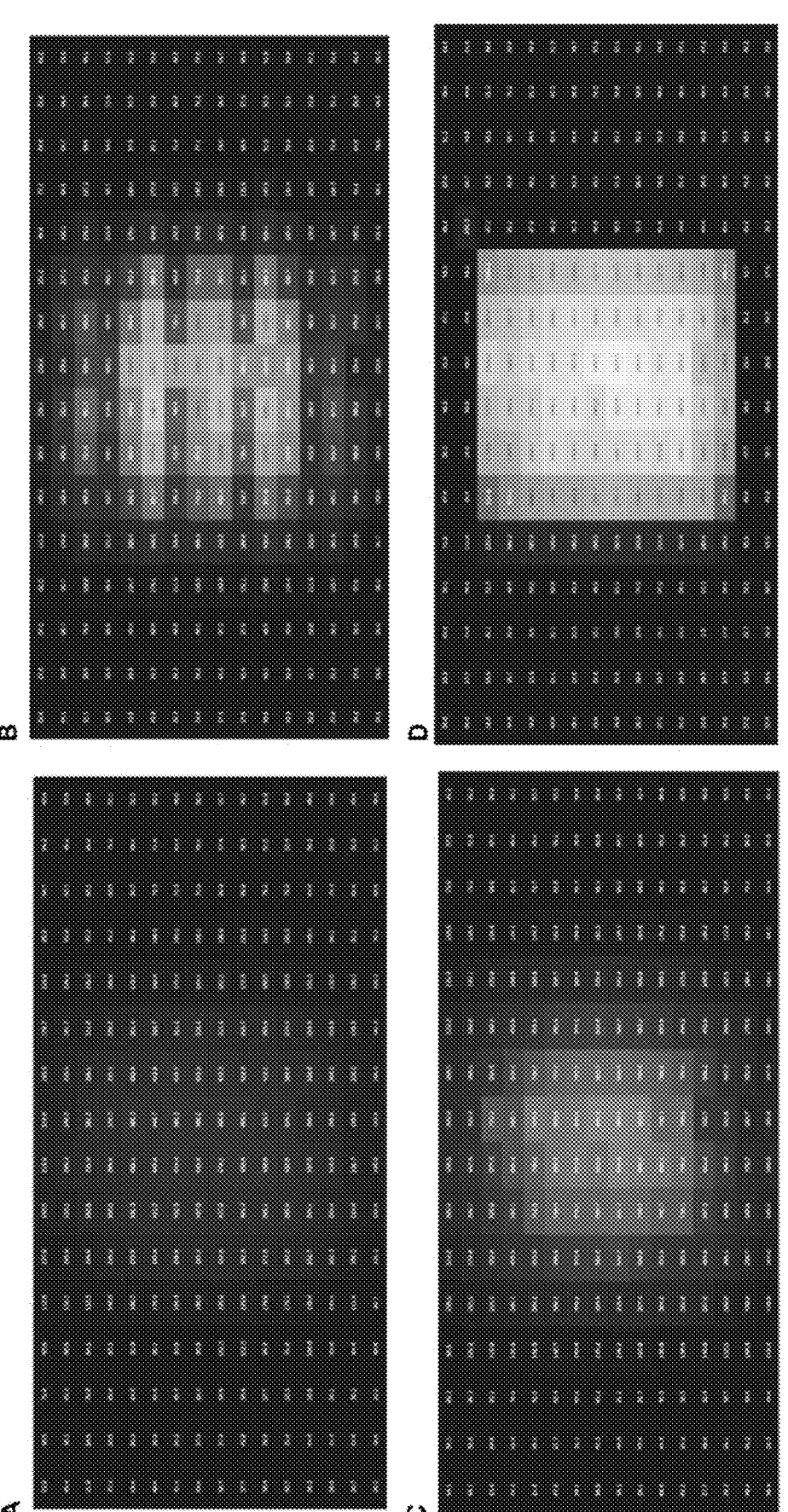
FIG. 4 are heat maps of different UV-C arrays taken at 30 cm separation distances. Panel A is the heatmap for an array with no diffuse reflective material. Panel B is the heatmap for a specular array with four UV-C lamps. Panel C is the heatmap for a diffuse array (i.e., the bottom surface of the array frame is covered with an ePTFE sheet) with no flexible reflectors (i.e., it is an incomplete irradiance chamber). Panel D is the heatmap for an exemplary FDRSC device of the present disclosure. The dark areas outside the bright squares indicate the area outside the irradiance zone/chamber. The brighter squares indicate higher irradiance values.

To compare the uniformity and intensity of the present FDRSC device as compared to a UV-C devices without diffusive-reflective chambers or UV-C devices with specular arrays (i.e., arrays with highly reflective, non-diffuse surfaces, such as aluminum), planar irradiance heatmaps at 30 cm separation distance were created for the FDRSC device and compared to heatmaps obtained from a four-UV-C lamp array with no diffusive-reflective covering (i.e., no ePTFE), an FDRSC array with no flexible reflectors (i.e., incomplete chamber), and a four-UV-C lamp specular array (i.e., rigid aluminum reflector). Irradiance data was collected by a UV-C sensor for 256 points and used to create a heat map where the bright squares indicate high irradiance readings and the dark squares indicate low irradiance readings. As shown in FIG. 4, the FDRSC device (panel D) produced the highest and yet most uniform irradiance intensity to the plant surfaces contained under the array as compared to the array with no ePTFE (panel A) and the array with no flexible reflectors (panel C). The specular array (panel B) showed the high variability. Thus, the treatment times with the specular array would have to be increased to provide the surfaces in the low irradiance gaps with sufficient UV-C dosage, but an increased UV-C dosage in these areas would cause excessive irradiance to the plant surfaces indicated by the irradiance hotspots. These hotspots are inefficient and can damage plant surfaces. The FDRSC device produced high reflectivity and uniformity under the FDRSC array (the areas outside the bright squares represent areas outside of the irradiance chamber).

Figures 5, 6:
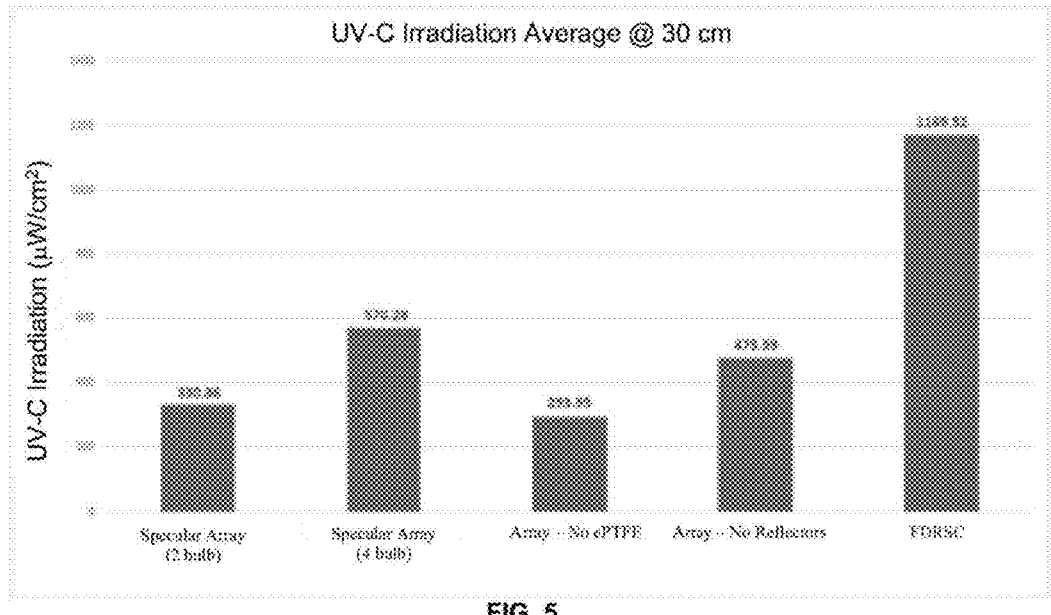
FIG. 5 is a bar graph showing the average UV-C irradiation for a specular array with 2 UV-C lamps (left bar), a specular array with 4 UV-C lamps (second bar from left), an array with no diffuse reflective material ("No ePTFE"; middle bar), a diffuse array frame with no flexible reflectors (second bar from right), and an FDRSC device (right bar). The y-axis represents average UV-C irradiation in $\mu W/cm^2$.
FIG. 6 is a line graph showing the horizontal UV-C irradiance plot for an array with no diffuse reflective material (square; bottom group), a diffuse array frame with no flexible reflectors (diamond; middle group), and an FDRSC device (circle; top group). The y-axis is the irradiance intensity, whereas the x-axis is the x or horizontal position of the UV-C reading.

The average UV-C irradiance was calculated for the area within the irradiance chamber of an FDRSC device and compared to a two UV-C lamp specular array, a four UV-C lamp specular array, an array with no diffusive reflector material (no ePTFE), and a diffuse array with no flexible reflectors (incomplete chamber). As shown in FIG. 5, the specular array with two lamps provided an average irradiance similar to the four lamp array with no diffusive reflector material. The specular four lamp array focused the irradiance and achieved a higher average than the diffuse array with no flexible reflectors (incomplete chamber)—likely due to less dispersion of the light. Adding the flexible reflectors on four sides provided the array with the diffuse reflective chamber and dramatically increased the average irradiance of the FDRSC device.

As shown in FIG. 6, the irradiance values in the horizontal orientation along the length of the array revealed less uniformity in the array with no diffuse reflector material (bottom group) than either the diffuse array with no reflectors (middle group) or the FDRSC device (top group).

Figure 7:
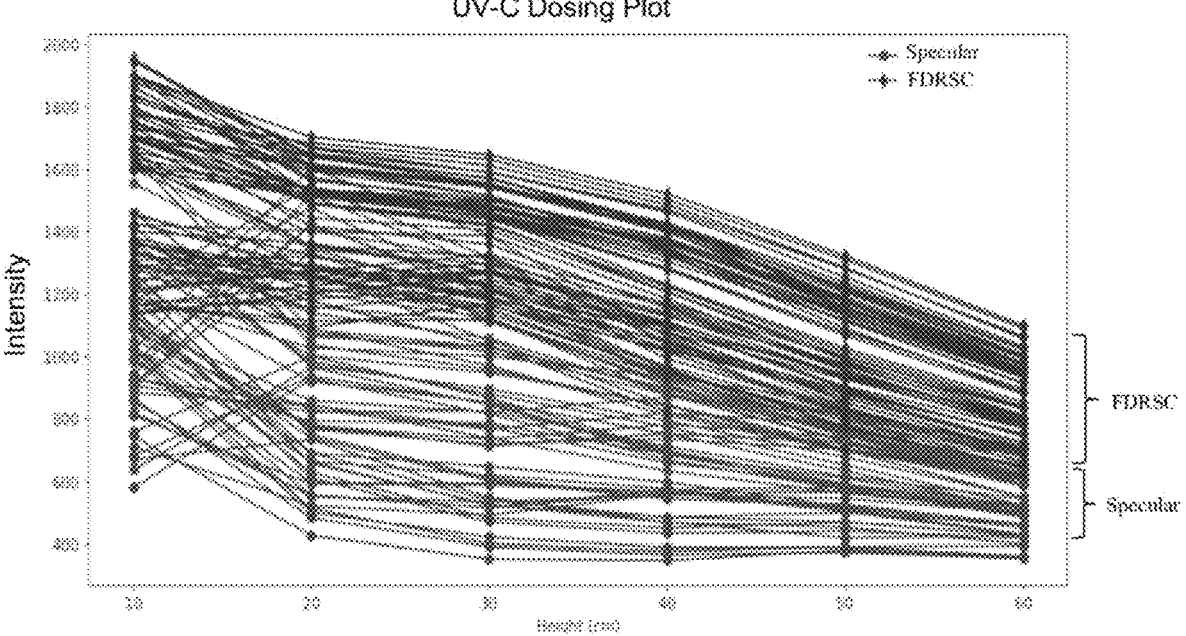
FIG. 7 is a line graph showing the vertical UV-C irradiance plot for a specular array (circle; bottom lines) and an FDRSC device (diamond; top lines). The y-axis is the irradiance intensity, whereas the x-axis is the height (cm) of the UV-C reading.

Finally, the analysis of the irradiance values in the vertical direction showed an increase in uniformity with the FDRSC device as compared to the four UV-C lamp specular array (see FIG. 7). The lines in FIG. 7 represent how the irradiance varied for individual sensors as their distance increased away from the lamps. At a single distance, if the points are spread across a wide range of intensities, then there is less uniformity in the treatment area. For the FDRSC device, the irradiance values were not only higher in intensity, but also spread over a narrower range of intensity values for each height as compared to the four UV-C lamp specular array (compared top group with bottom group).

We claim:

1. A device for reducing or preventing a pest or pathogen infestation on a plant or plant part, the device comprising an array frame having a top surface and a bottom surface, one or more light sources affixed to the array frame proximate to the bottom surface of the array frame, a first diffuse reflective material, and one or more flexible or semi-flexible reflectors having an inner surface and an outer surface, wherein each reflector is affixed to the array frame, wherein:

a) the first diffuse reflective material is disposed on the bottom surface of the array frame and positioned between the bottom surface of the array frame and each of the one or more light sources;

b) the one or more light sources are configured to emit light having a spectral wavelength in the range from about 100 nm to about 280 nm;

c) each of the one or more reflectors comprise a second diffuse reflective material on at least the inner surface; and d) the bottom surface of the array frame and inner surface of each of the one or more reflectors form an irradiance chamber configured for diffuse reflection of light and that is open on at least one end for receiving one or more plants or plant parts; wherein light emitted from the one or more light sources is diffusely reflected by the irradiance chamber and contacts the one or more plants or plant parts to reduce or prevent a pest or pathogen infestation on the one or more plants or plant parts.

2. The device of claim 1, wherein:

the first diffuse reflective material and the second diffuse reflective material are each selected from the group consisting of non-absorbing powder, fibrous material, polycrystalline material, white diffusing paint based on barium sulphate, sintered polytetrafluoroethylene, expanded polytetrafluoroethylene (ePTFE), and any combination thereof.

3. The device of claim 1, comprising at least four reflectors, wherein each reflector is attached to and extends from an end of the array frame to form an irradiance chamber with a top end, a front, a back, two sides, and an open bottom end for receiving the plants or plant parts.

4. The device of claim 3, wherein the side reflectors have a greater height than the front and back reflectors.

5. The device of claim 3, wherein the front and back reflectors include at least one vertical cut.

6. The device of claim 1, wherein the one or more light sources are configured to emit ultraviolet C (UV-C) light having a spectral wavelength in the range from about 220 nm to about 230 nm, or about 250 nm to about 260 nm.

7. The device of claim 1, wherein the one or more light sources are fluorescent germicidal lamps.

8. The device of claim 1, further comprising at least one distance detector disposed on the bottom surface of the array frame and one or more light sensors disposed on the bottom surface of the array frame, wherein the at least one distance detector is a stereo camera, the one or more light sensors are UV-C sensors, or both.

9. The device of claim 8, further comprising a dosing control system, wherein the dosing control system comprises one or more user-defined dosing parameters and a dosing controller, wherein the one or more user-defined dosing parameters are selected from the group consisting of dosing amount, target dosing, minimum dosing distance, minimum dosing time, and any combination thereof, and wherein the dosing control system:

a) receives electrical signals from the at least one distance detector to create a treatment contour profile; and b) receives electrical signals from the one or more light sensors to create an volumetric irradiance profile;

wherein the dosing controller combines data from the treatment contour profile and data from the volumetric irradiance profile to create an irradiance heatmap, and further converts data from the irradiance heatmap to determine treatment distance, treatment time, or both treatment distance and treatment time based on the one or more user-defined dosing parameters.

10. The device of claim 9, further comprising:

an autonomous vehicle, wherein the device is attached to a support member of the autonomous vehicle, wherein the autonomous vehicle is a land vehicle comprising one or more wheels, and wherein the support member is further attached to an adjustable vertical mount on the autonomous vehicle.

11. The device of claim 10, wherein the autonomous vehicle comprises a central processing unit (CPU) configured to receive electrical signals from the dosing control system, wherein:

a. the treatment time is communicated from the dosing control system to the CPU of the autonomous vehicle to cause rotation of the wheels to increase or decrease in velocity; or b. the treatment distance is communicated from the dosing control system to the CPU of the autonomous vehicle to cause the adjustable vertical mount to raise or lower the device; or c. both a) and b).

12. The device of claim 1, wherein the first diffuse reflective material and the second diffuse reflective material are at least about 80% reflective of UV-C light.

13. The device of claim 12, wherein the first diffuse reflective material and the second diffuse reflective material are at least about 90% reflective of UV-C light.

14. The device of claim 13, wherein the first diffuse reflective material and the second diffuse reflective material are at least about 95% reflective of UV-C light.

15. A method of treating or preventing pest or pathogen infestation on a plant or plant part, the method comprising:

a. providing the plant or plant part;

b. placing the device of claim 1 over the plant or plant part such that the plant or plant part is received within the irradiance chamber of the device; and c. contacting the plant or plant part with UV-C light emitted from the one or more light sources of the device at a target dosage amount for a period of time of at least about 1 sec; wherein the contacting of the plant or plant part with the UV-C light reduces or prevents infestation from pests or pathogens.

16. The method of claim 15, wherein the pest or pathogen is selected from the group consisting of fungi, bacteria, insects, mollicutes, viruses, protozoa, viroids, and any combination thereof.

17. The method of claim 15, wherein the plant or plant part is selected from the group consisting of asparagus, barley, beans, beets, blueberries, broccoli, cabbage, canola, cauliflower, celery, cranberries, corn, cotton, feed grains, flowers, garlic, grapes, lentils, lettuce, mushrooms, oats, peanuts, peas, peppers, potatoes, pumpkins, rice, sorghum, soybeans, spinach, squash, strawberries, sugar cane, sweet potatoes, tobacco, tomatoes, turnips, watermelon, and wheat.

18. The method of claim 15, wherein the target dosage is at least about 1 J/m$^2$.

19. The method of claim 18, wherein the target dosage is at least about 5 J/m$^2$.

20. The method of claim 15, wherein the pests or pathogens are reduced by at least 10% following contact of the plant or plant part with the UV-C light for the period of time.

21. The method of claim 15, wherein the contacting step is followed by a dark period.

22. The method of claim 15, further comprising measuring one or more parameters of pest or pathogen infestation, wherein the measuring step is prior to, following, or both prior to and following the contacting step, wherein the one or more parameters of pest or pathogen infestation are selected from the group consisting of leaf rust, stem rust, sclerotinia, spots, damping, chlorosis, lesions, bacterial oozing, fruit rust, cankers, crown galls, Sheperd's crook stem ends, mosaic leaf patters, crinkled leaves, yellowed leaves, plant stunting, mycelium growth, mold growth, fruiting bodies, bacterial odors, stem rot, blight, fungal rings, water soaking, bacterial streaming, stunted growth, and wilting.

23. The device of claim 1, wherein the reflectors comprise rubber, flexible plastic, or cloth coated with the second diffuse reflective material.

24. The device of claim 1, wherein the reflectors have a Modulus of Elasticity from about 0.001 to about 5 GPa.

25. The device of claim 1, wherein said disposal of the first diffuse reflective material on the array frame produces angled portions of the first diffuse reflective material that taper towards either side of at least one light source.

* * * * *